United States Patent [19]

Russell et al.

[11] Patent Number: 4,939,137

[45] Date of Patent: Jul. 3, 1990

[54] RING-FUSED THIENOPYRIMIDINEDIONE DERIVATIVES

[75] Inventors: Ronald K. Russell, Titusville; Richard A. Rampulla, Whitehouse Station, both of N.J.

[73] Assignee: Ortho Pharmaceutical Corporation, Raritan, N.J.

[21] Appl. No.: 372,505

[22] Filed: Jun. 28, 1989

[51] Int. Cl.$^5$ .................... A61K 31/55; C07D 495/14
[52] U.S. Cl. .................................. 514/183; 514/214; 514/220; 514/267; 540/460; 540/461; 540/497; 540/520; 544/250
[58] Field of Search ............... 514/183, 220, 214, 267; 540/460, 461, 497, 520; 544/250

[56] References Cited

U.S. PATENT DOCUMENTS 4,670,560 6/1987 Press et al. .......................... 544/278
4,703,120 10/1987 Press .................................. 544/278

*Primary Examiner*—Robert T. Bond
*Attorney, Agent, or Firm*—Benjamin F. Lambert

[57] ABSTRACT

The synthesis of ring-fused thienopyrimidinedione derivatives is described. The novel ring-fused thienopyrimidinedione derivatives are generally vasodilating agents and antihypertensive agents and as such are useful as cardiovascular agents.

18 Claims, No Drawings

RING-FUSED THIENOPYRIMIDINEDIONE DERIVATIVES

BACKGROUND OF THE INVENTION

The cardiovascular disorder, hypertension, afflicts between 10–20% of the adult population and is a major risk factor in many forms of other cardiovascular disease [N. M. Kaplan, Arch. Intern. Med., 143, 255(1983)]. One way to reduce the blood pressure of a hypertensive patient is to dilate the cardiovascular system by administering an alpha-1 antagonist such as the drug Prazosin ("Prazosin: Pharmacology, Hypertension and Congestive Heart Failure,", M. D. Rawlins, Ed., 1981). Another way to treat hypertension is to administer ketanserin, [3-[2-[4-(4-fluorobenzoyl)piperidin-1-yl]ethyl]-2,4-(1H,3H)quinazolinedione], as described at the proceedings of the 10th Scientific Meeting of the International Society of Hypertension, [J. Cardiovasc. Pharmacol. (1985), 7 (Suppl 7)]. This drug is a serotonin antagonist [for a review of serotonin's role in the vascular system, see D. S. Houston and P. M. Vanhoutte, Drugs, 31, 149 (1986)], and this class of drugs has also been shown to inhibit platelet aggregation, tracheal smooth muscle contraction, gastrointestinal smooth muscle contraction, and anxiety disorders. [P. A. J. Janssen, TIPS, 4, 198 (1983); P. A. J. Janssen, *J. Cardiovasc. Pharmacol.* 1985, 7 (Suppl 7), S2; P. R. Saxena, et al., TIPS, 8, (1986)].

A compound which shows activity in the established Spontaneous Hypertensive Rat (SHR) model (or alpha-1 receptor binding) is potentially an agent for use in hypertension. Likewise, a compound which shows activity towards the serotonin receptor should be an agent for an agent for use in gastric motility, or an agent to modify the state of tension and anxiety.

SUMMARY OF THE INVENTION

The present invention is directed to ring-fused thienopyrimidine compounds of the formula

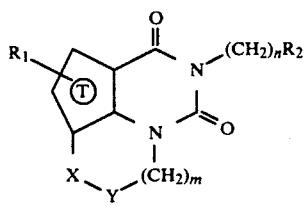

where
X may be C=O or CHOR$_3$ or C=NOR$_4$ or CHNHR$_3$ when Y is CH$_2$
X and Y together may be CH=CH and Y may be NH when X is C=O

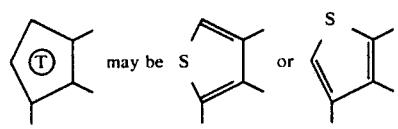

R$_1$ may be hydrogen, halogen, nitro or C$_1$-C$_3$ alkyl
R$_2$ may be

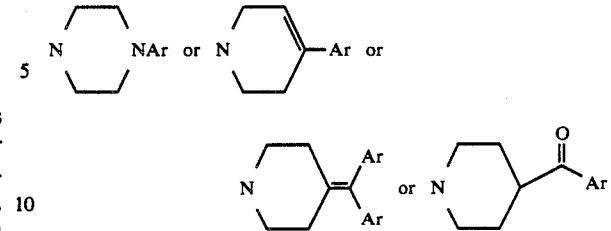

R$_3$ may be hydrogen, C$_1$-C$_3$ alkyl or COR$_5$;
R$_4$ may be hydrogen or C$_1$-C$_6$ alkyl;
R$_5$ may be C$_1$-C$_6$ alkyl, phenyl or phenyl substituted by halogen, C$_1$-C$_6$ alkyl, C$_1$-C$_3$ alkoxy, nitro, CF$_3$, amino or C$_1$-C$_6$ dialkylamino;
Ar may be phenyl or substituted phenyl as described above
m may be 1-5; and
n may be 2-6.

These novel compounds are generally vasodilating agents and antihypertensive agents and as such are useful as cardiovascular agents.

DETAILED DESCRIPTION OF THE INVENTION

The invention in its broadest aspects relates to ring-fused thienopyrimidinedione derivatives which have cardiovascular activity, such as antihypertensive activity or general vasodilator activity in mammals. The thienopyrimidine-3,5-dione derivatives of the invention demonstrating a cardiovascular activity are shown by the formula above. The thienopyrimidine-3,5-dione derivatives which have a cardiovascular activity all contain a nitrogen at the 4-position of the pyrimidine ring which is substituted by the group

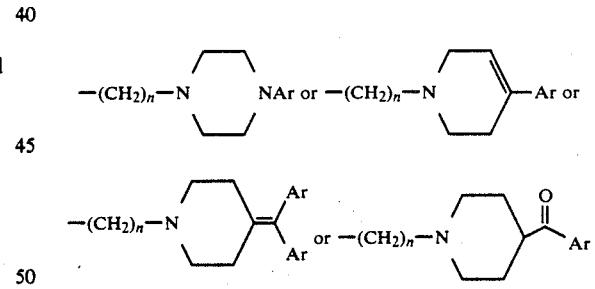

where Ar and n are as defined above.

The preferred compounds of the present invention are those wherein X is C=O or CHOR$_3$ or C=NOR$_4$ or CHNHR$_3$
when Y is CH$_2$ or X and Y are CH=CH and where Y may be NH
when X is C=O

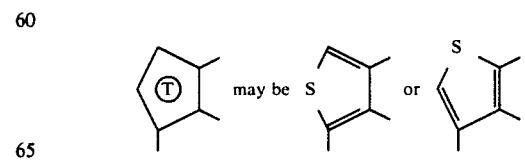

R$_1$ is hydrogen or C$_1$-C$_3$ alkyl
R$_2$ is

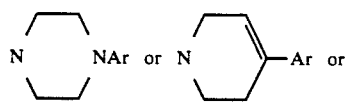
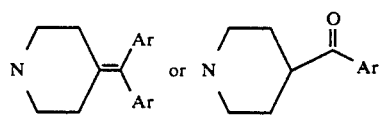
$R_3$ is hydrogen or $COR_5$;
$R_4$ is hydrogen or methyl;
$R_5$ is $C_1$–$C_6$ alkyl or phenyl or phenyl substituted by a 4-chloro or 4-methoxy substituent
Ar is phenyl or phenyl substituted by halogen, methyl, methoxy, or $CF_3$;
m is 1–3; and
n is 2–6.
The compounds of this invention are prepared as follows:
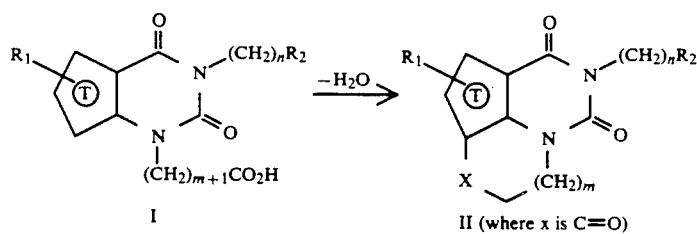
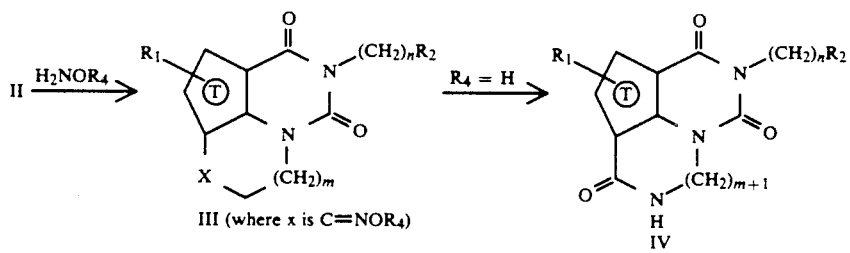
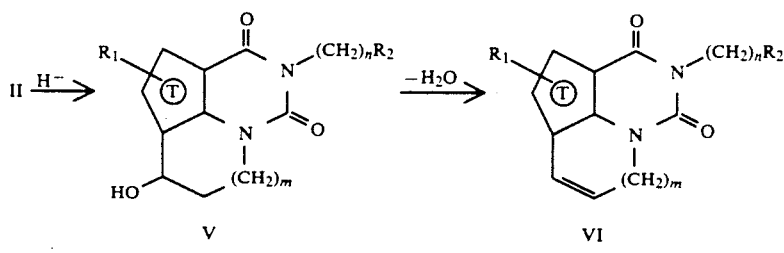
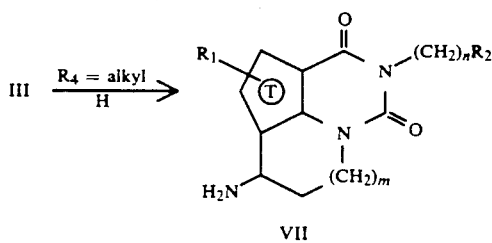
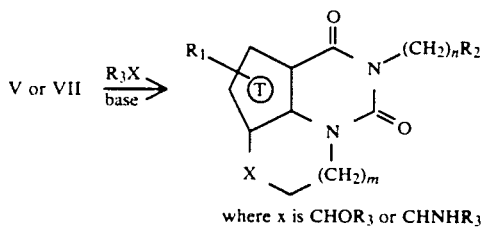

V or VII $\xrightarrow{R_5COCl}{\text{base}}$ 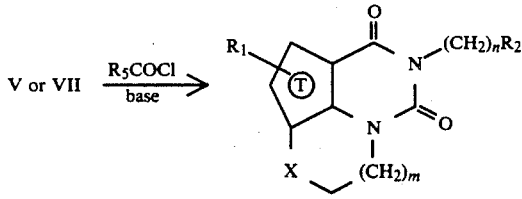

where x is CHOCOR$_5$ or CHNHCOR$_5$

The thienopyrimidine-2,4-dione starting materials I were prepared by either the method of J. Press and R. Russell (U.S. Pat. No. 4,670,560) or by the method of J. Press and R. Russell, (U.S. patent application Ser. No. 168,199, filed Mar. 15, 1988) the subject matter of which is incorporated herein by reference. These carboxylic acids were cyclized to the ketones II (X is C=O) with strong acid such as polyphosphoric acid, sulfuric acid, polyphosphate ester or methanesulfonic acid/phosphorous pentoxide (10/1) [P. E. Eaton, G. R. Carlson, and J. T. Lee, *J. Org. Chem.*, 38, 4071 (1973)] either without or in an inert solvent such as chloroform, dichloromethane, or toluene at 25° to 100° C. for 2 to 16 hours. These crystalline ketones II were converted to their oximes III by mixing with commercially available hydroxylamine, o-methylhydroxylamine, o-ethylhydroxylamine among others in an inert solvent such as methanol or ethanol at reflux for 2 to 24 hours. When hydroxylamine hydrochlorides were used, a base such as sodium acetate, sodium hydroxide or potassium hydroxide was added.

The oximes III (R$_4$=H) were ring-expanded to IV by employing the usual Beckmann rearrangement conditions such as PCl$_5$ in toluene, concentrated sulfuric acid, polyphosphoric acid or methanesulfonic acid/phosphorous pentoxide, among others.

These ring-fused structures (X is C=O) were reduced with a hydride reagent such as sodium borohydride, lithium borohydride, or lithium tri-tert-butoxyaluminohydride, among others, in an inert solvent such as methanol, ethanol or tetrahydrofuran preferably under an inert atmosphere such as nitrogen or argon at 25° to 40° C. for 6 to 18 hours.

The alcohols V were dehydrated by the usual procedures such as strong acid (e.g., sulfuric acid or polyphosphoric acid) or acetic acid/acetic anhydride at reflux for 12 hours or methanesulfonyl chloride/triethylamine in dichloromethane at reflux for 12 hours, among others, to produce the olefins VI.

The oximes III (R$_4$=alkyl) were reduced to amines VII with a hydride reagent such as diborane, sodium borohydride, lithium borohydride, or lithium tri-tert-butoxyaluminohydride, among others, in an inert solvent such as tetrahydrofuran, dimethoxyethane, methanol or ethanol preferably under an inert atmosphere such as nitrogen or argon at 25° to 67° C. for 2 to 18 hours.

These alcohols V or amines VII were then alkylated with alkyl halides such as methyl iodide, isopropyl iodide, butyl bromide, or benzyl bromide, among others, in an inert solvent such as tetrahydrofuran, dioxane, dimethoxyethane, or dimethylformamide in the presence of a base such as sodium hydride, sodium carbonate, or potassium carbonate, preferably under an inert atmosphere such as nitrogen or argon. The esters or amides of V or VII, respectively, were prepared by mixing with the appropriate acid halide such as acetyl chloride, butanoyl chloride, hexanoyl chloride, isobutanoyl chloride, benzoyl chloride, 4-chlorobenzoyl chloride, 4-methoxybenzoyl chloride, or methyl 4-(chloroformyl) butyrate, among others, in an inert solvent such as dichloromethane, chloroform, tetrahydrofuran or dimethoxyethane in the presence of a base such as triethylamine or pyridine or 4-dimethylaminopyridine.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenteral, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain dosage unit, e.g., tablet, capsule, powder, injection, teaspoonful and the like, from about 0.5 to about 100 mg/kg, and preferably from about 1 to about 5 mg/kg of the active ingredient.

The following examples describe the invention in greater particularity and are intended to be a way of illustration but not limiting the invention.

EXAMPLE 1

3,4,5,7,8,9-Hexahydro-4-[2-[4-(2-methoxyphenyl)piperazin-1-yl]ethyl]thieno[4,3,2-de]pyrido[1,2c]pyrimidine-3,5,9-trione A chloroform solution of 20 g (51.6 mmole) of 3-[2-[4-(2-methoxyphenyl)piperazin-1-yl]ethyl]thieno[3,4-d]pyrimidine-2,4-dione (J. Press and R. Russell, U.S. Pat. No. 4,670,560) was mixed with 0.5 equivalent of Triton B (40% in MeOH) and methyl acrylate (44.56 g, 0.516 mol) at reflux for one hour. Another 0.5 equivalents of Triton B was added and warming to reflux was continued for an additional hour. After the solvents had been removed in vacuo, the dark residue was purified by flash silica gel chromatography using $CH_2Cl_2$ and then 1% MeOH in $CH_2Cl_2$. There was obtained 18.43 g (75%) of the known (J. Press and R. Russell, U.S. Pat. No. 4,670,560)methyl 3-[3-[2-[4-(2-methoxyphenyl)piperazin-1-yl]ethyl]-2,4-dioxothieno[3,4-d]pyrimidin-1-yl]propanoate.

The above ester (3.08 g, 6.52 mmol) was suspended in methanol and water (5 ml) and treated with 0.568 mL (6.8 mmol) of 50% NaOH. After the mixture had been heated for 2 hours, water was added and the pH was adjusted to 6-7 with 2N HCl. The aqueous solution was extracted with $CH_2Cl_2$ and the combined extracts were washed with brine and dried ($Na_2SO_4$). Solvent removal produced a light yellow foam which was crystallized from hot ethanol to produce 857 mg (28.5%) of 3-[3-[2-[4-(2-methoxyphenyl)piperazin-1-yl]ethyl]-2,4-dioxothieno[3,4-d]pyrimidin-1-yl]propanoic acid as a white solid, mp 186°-187.5° C.

Theor. $C_{22}H_{26}N_4O_5S$: C,57.62:H,5.72;N,12.22.
Found: C,57.54;H,5.71;N,12.27.

The above acid (7.76 g, 17 mmol) was vigorously stirred in $P_2O_5/CH_3SO_3H$ [Eaton's reagent; P. E. Eaton, G. R. Carlson, and J. T. Lee, *J. Org., Chem.*, 38, 4071 (1973)] at room temperature under nitrogen for 2 hours. After this red solution had been carefully poured into ice-water, the pH of the solution was carefully adjusted to 8 with concentrated $NH_4OH$ at 40°-45° C. The solid was isolated and purified by flash silica gel chromatography using 1% MeOH in $CH_2Cl_2$. The material obtained from the column was triturated with ether to produce 4.58 g (61.2%) of the title compound as a yellow crystalline solid, mp 158°-160° C.

Theor. $C_{22}H_{24}N_4O_4S$: C,59.38;H,5.49;N,12.72.
Found: C,59.74;H,5.44;N,12.69.

EXAMPLE 2

3,4,5,7,8,9-Hexahydro-4-[2-[4-(2-methylphenyl)piperazin-1-yl]ethyl]thieno[4,3,2-de]pyrido[1,2-c]pyrimidine-3,5,9-trione The title compound was produced following the procedure of Example 1 using 15.72 g (42.4 mmol) of 3-[2-[4-(2-methylphenyl)piperazin-1-yl]ethyl]thieno[3,4-d]pyrimidine-2,4-dione to produce methyl 3-[3-[2-[4-(2-methylphenyl)piperazin-1-yl]ethyl]-2,4-dioxothieno[3,4-d]pyrimidin-1-yl]propanoate in 69.8% yield (13.52 g) after recrystallization from $CH_2Cl_2$/hexane to afford a white solid, mp 149°-150° C.

Theor. $C_{23}H_{28}N_4O_4S$: C,60.50;H,6.18;N,12.27.
Found: C,60.28;H,6.25;N,12.24.

The above ester (11.98 g, 26.2 mmol) was hydrolyzed to its corresponding carboxylic acid sodium salt as described in Example 1. There was obtained 7.84 g (67.5%) of 3-[3-[2-[4-(2-methylphenyl)piperazin-1-yl]ethyl-2,4-dioxothieno[3,4-d]pyrimidin-1-yl]propanoic acid sodium salt as a cream-colored solid, mp 152° C. (softens), 163°-166° C. (dec).

Theor. $C_{22}H_{25}N_4NaO_4S.H_2O$: C,54.76;H,5.84;N,11.61.
Found: C,54.66;H,5.90;N,11.43.

The above acid sodium salt (6.27 g. 13.0 mmol) was cyclized as described in Example 1. There was obtained 3.62 g (60.2%) of the title compound after recrystallization from $CH_2Cl_2$/hexane to afford a yellow solid, mp 156.5°-157.5° C.

Theor. $C_{22}H_{24}N_4O_3S$: C,62.24;H,5.70;N,13.20.
Found: C,62.52;H,5.72;N,13.18.

EXAMPLE 3

4-[2-[4-(2-Chlorophenyl)piperazin-1-yl]ethyl]3,4,5,7,8,9-hexahydrothieno[4,3,2-de]pyrido[1,2-c]pyrimidine-3,5,9-trione The title compound was produced following the procedure of Example 1 using 20.2 g (51.7 mmol) of 3-[2-[4-(2-chlorophenyl)piperazin-1-yl]ethyl]thieno[3,4-d]pyrimidine-2,4-dione to produce methyl 3-[3-[2-[4-(2-chlorophenyl)piperazin-1-yl]ethyl]-2,4-dioxothieno[3,4-d]pyrimidin-1-yl]proponoate as a creamed-colored solid after recrystallization from $CH_2Cl_2$/hexane in 70.5% yield (17.38 g), mp 142.5°-144° C.

Theor. $C_{22}H_{25}ClN_4O_4S$: C,55.39;H,5.28;N,11.75.
Found: C,54.97;H,5.34;N,11.66.

The above ester (15.59 g., 32.7 mmol) was hydrolyzed to its corresponding carboxylic acid sodium salt as described in Example 1. There was obtained 14.57 g (94%) of 3-[3-[2-[4-(2-chlorophenyl)piperazin-1-yl]ethyl]-2,4-dioxothieno[3,4-d]pyrimidin-1-yl]propanoic acid sodium salt as a beige solid, mp 213°-223° C. (dec).

Theor. $C_{21}H_{22}ClN_4NaO_4S.H_2O$: C,50.15;H,4.82;N,11.14.
Found: C,50.21;H,4.68;N,11.10.

The above acid sodium salt (11.75 g, 23.4 mmol) was cyclized as described in Example 1. There was obtained 6.29 g (55%) of the title compound after recrystallization from $CH_2Cl_2$/hexane to afford a yellow solid, mp 183.5°-184.5° C.

Theor. $C_{21}H_{21}ClN_4O_3S$: C,56.68;H,4.76;N,12.59.
Found: C,56.72;H,4.76;N,12.41.

EXAMPLE 4

3,4,5,7,8,9-Hexahydro-4-[2-(4-phenylpiperazin-1-yl)ethyl]thieno[4,3,2-de]pyrido[1,2-c]pyrimidine-3,5,9-trione The title compound was produced following the procedure of Example 1 using 11.31 g (31.7 mmol) of 3-[2-(4-phenylpiperazin-1-yl)ethyl]thieno[3,4-d]pyrimidine-2,4-dione to produce methyl 3-[3-[2-(4-phenylpiperazin-1-yl]ethyl]-2,4-dioxothieno[3,4-d]pyrimidin-1-yl]propanoate in 84.9% yield (11.92 g) after recrystallization from $CH_2Cl_2$/hexane to afford a cream-colored solid, mp 133°-134.5° C.

Theor. $C_{22}H_{26}N_4O_4S$: C,59.71;H,5.92;N,12.66.
Found: C,59.51;H,6.01;N,12.76.

The above ester (9.83 g, 22.2 mmol) was hydrolyzed to its corresponding carboxylic acid sodium salt as described in Example 1. There was obtained 9.26 g (93%) of 3-[3-[2-(4-phenylpiperazin-1-yl)ethyl]-2,4-dioxothieno[3,4-d]pyrimidin-1-yl]propanoic acid sodium salt as a beige solid, mp 188° C. (softens), 199°-201° C. (dec).

Theor. $C_{21}H_{23}N_4NaO_4S$: C,55.99;H,5.15;N,12.44.
Found: C,55.65;H,5.44;N,12.30.

The above acid sodium salt (7.18 g, 15.9 mmol) was cyclized as described in Example 1. There was obtained 3.95 g (57.4%) of the title compound after recrystallization from $CH_2Cl_2$/hexane to afford a yellow solid, mp 178.5°-180° C.

Theor. $C_{21}H_{22}N_4O_3S$: C,61.44;H,5.40;N,13.65.
Found: C,61.40;H,5.39;N,13.53.

EXAMPLE 5

3,4,5,7,8,9-Hexahydro-4-[2-[4-(3-methoxyphenyl)piperazin-1-yl]ethyl]thieno[4,3,2-de]pyrido[1,2-c]pyrimidine-3,5,9-trione The title compound was produced following the procedure of Example 1 using 9.88 g (25.6 mmol) of 3-[2-[4-(3-methoxyphenyl)piperazin-1-yl]ethyl]-thieno[3,4-d]pyrimidine-2,4-dione to produce methyl 3-[3-[2-[4-(3-methoxyphenyl)piperazin-1-yl]ethyl]-2,4-dioxothieno[3,4-d]pyrimidin-1-yl]propanoate in 68.4% yield (8.28 g) after recrystallization from $CH_2Cl_2$/hexane to afford a cream-colored solid, mp 136°–137° C.

Theor. $C_{23}H_{28}N_4O_5S$: C,58.45;H,5.97;N,11.86.
Found: C,58.15;H,6.03;N,11.75.

The above ester (6.78 g, 14.3 mmol) was hydrolyzed to its corresponding carboxylic acid as described in Example 1. There was obtained 2.3 g of crude 3-[3-[2-[4-(3-methoxyphenyl)piperazin-1-yl]ethyl]-2,4-dioxothieno[3,4-d]pyrimidin-1-yl]propanoic acid. The aqueous was condensed in vacuo and the residue was leached with hot EtOH. There was obtained a total of 4.41 g (67%) of a light-yellow foam.

The above crude acid (2.68 g, 5.84 mmol) was cyclized as described in Example 1. There was obtained 1.89 g (73.4%) of the title compound after recrystallization from chloroform/hexane to afford a canary-yellow solid, mp 190°–191° C.

Theor. $C_{22}H_{24}N_4O_4S$: C,59.98;H,5.49;N,12.72.
Found: C,59.74;H,5.51;N,12.60.

EXAMPLE 6

4-[2-[4-(3-Trifluoromethylphenyl)piperazin-1-yl]ethyl]-3,4,5,7,8,9-hexahydrothieno[4,3,2-de]-pyrido[1,2-c]pyrimidine-3,5,9-trione The N-(3-carbomethoxythien-4-yl)-N'-(2-chloroethyl)urea (10.02 g, 38 mmol) (J. Press and R. Russell, U.S. Pat. No. 4,670,560) was mixed with 20.36 g (76 mmol) of 1-(3-trifluoromethylphenyl)piperazine hydrochloride, 12.82 g (0.153 mol) of sodium bicarbonate, and 2.86 g (19 mmol) of sodium iodide in 80 mL of 2-propanol at reflux for 18 hours. After water had been added and the 2-propanol removed in vacuo, the aqueous mixture was extracted with $CH_2Cl_2$. The combined extracts were washed with water and brine and dried ($MgSO_4$). After the solvent had been removed in vacuo, the residue was purified by flash silica gel chromatography using 1–3% MeOH in $CH_2Cl_2$. There was obtained 9.5 g (59%) of desired product. A portion of this material was recrystallized from $CH_2Cl_2$/ether to afford a tan solid, mp 182°–184° C.

Theor. $C_{19}H_{19}F_3N_4O_2S$: C,53.76;H,4.51;N,13.20.
Found: C,53.49;H,4.54;N,13.26.

The above compound (8.25 g, 19 mmol) was reacted with methyl acrylate as described in Example 1 to produce methyl 3-[3-[2-[4-(3-trifluoromethylphenyl)piperazin-1-yl]ethyl]-2,4-dioxothieno[3,4-d]pyrimidin-1-yl]propanoate in 38% yield (3.72 g) after recrystallization from $CH_2Cl_2$/hexane to afford a creamed-colored solid, mp 87°–88° C.

Theor. $C_{23}H_{25}F_3N_4O_4S$: C,54.11;H,4.94;N,10.98.
Found: C,54.26;H,4.97;N,11.20.

The above ester (3.15 g, 6 mol) was hydrolyzed to its corresponding carboxylic acid as described in Example 1. There was obtained 3.09 g (100%) of 3-[3-[2-[4-(3-trifluoromethylphenyl)piperazin-1-yl]ethyl]-2,4l-dioxothieno[3,4-d]pyrimidin-1-yl]propanoic acid.

The above crude acid was cyclized as in Example 1. There was obtained 0.33 g (11%) of the title compound after recrystallization from $CH_2Cl_2$/hexane to afford a tan solid, mp 158°–160° C.

Theor. $C_{22}H_{21}F_3N_4O_3S$: C,55.22;H,4.42;N,11.71.
Found: C,55.26;H,4.46;N,11.81.

EXAMPLE 7

4-[2-[4-(3-Chlorophenyl)piperazin-1-yl]ethyl]-3,4,5,7,8,9-hexahydrothieno[4,3,2-de]pyrido[1,2-c]pyrimidine-3,5,9-trione The title compound was produced following the procedure of Example 1 using 9.77 g (25 mmol) of 3-[2-[4-(3-chlorophenyl)piperazin-1-yl]ethyl]thieno[3,4-d]pyrimidine-2,4-dione to produce methyl 3-[3-[2-[4-(3-chlorophenyl)piperazin-1-yl]ethyl]-2,4-dioxothieno[3,4-d]pyrimidin-1-yl]propanoate in 37% yield (4.4 g) after recrystallization from $CH_2Cl_2$/hexane to produce a cream-colored solid, mp 150° C.

Theor. $C_{22}H_{25}ClN_4O_4S$: C,55.39;H,5.28;N,11.75.
Found: C,55.35;H,5.28;N,11.64.

The above ester (3.52 g, 7.4 mmol) was hydrolyzed to its corresponding carboxylic acid as described in Example 1. There was obtained 1.51 g (44.1%) of 3-[3-[2-[4-(3-chlorophenyl)piperazin-1-yl]ethyl]-2,4-dioxothieno[3,4-d]pyrimidin-1-yl]propanoic acid.

The above crude acid (3.21 g, 6.9 mmol) was cyclized to the title compound in 64% yield (1.97 g) after recrystallization from $CH_2Cl_2$/hexane to afford a light yellow solid, mp 187°–191° C.

Theor. $C_{21}H_{21}ClN_4O_3S$: C,56.68;H,4.76;N,12.59.
Found: C,56.36;H,4.85;N,12.45.

EXAMPLE 8

3,4,5,7,8,9-Hexahydro-4-[2-[4-(4-methoxyphenyl)piperazin-1-yl]ethyl]thieno[4,3,2-de]pyrido[1,2-c]pyrimidine-3,5,9-trione The title compound was produced following the procedure of Example 1 using 11.98 g (31 mmol) of 3-[2-[4-(4-methoxyphenyl)piperazin-1-yl]ethyl]-thieno[3,4-d]pyrimidine-2,4-dione to produce methyl 3-[3-[2-[4-(4-methoxyphenyl)piperazin-1-yl]ethyl]-2,4-dioxothieno[3,4-d]pyrimidin-1-yl]propanoate in 93.7% yield (11.23 g) after recrystallization from $CH_2Cl_2$/hexane to afford an off-white solid, mp 151°–152° C.

Theor. $C_{23}H_{28}N_4O_5S$: C,58.45;H,5.97;N,11.86.
Found: C,58.17;H,5.83;N,11.55.

The above ester (9.81 g, 21.4 mmol) was hydrolyzed to its corresponding carboxylic acid sodium salt as described in Example 1. There was obtained 8.56 g (90%) of 3-[3-[2-[4-(4-methoxyphenyl)piperazin-1-yl]ethyl]2,4-dioxothieno[3,4-d]pyrimidin-1-yl]propanoic acid sodium salt as a cream-colored solid, mp 186° C. (softens), 220°–223° C. (dec).

Theor. $C_{22}H_{25}N_4NaO_5S.\frac{1}{2}H_2O$: C,53.97;H,5.76;N,11.44.
Found: C,54.01;H,5.61;N,11.32.

The above acid sodium salt (7.32 g, 15.2 mmol) was cyclized as described in Example 1. There was obtained 4.18 g (59.4%) of the title compound after recrystallization from chloroform/hexane to afford an orange solid, mp 195°–196° C.

Theor. $C_{22}H_{24}N_4O_4S$: C,59.98;H,5.49;N,12.72.
Found: C,59.89;H,5.42;N,12.74.

EXAMPLE 9

3,4,5,7,8,9-Hexahydro-4-[2-[4-(4-fluorophenyl)piperazin-1-yl]ethyl]thieno[4,3,2-de]pyrido[1,2-c]pyrimidine-3,5,9-trione The title compound was produced following the procedure of Example 1 using 14.68 g (39.2 mmol) of 3-[2-[4-(4-fluorophenyl)piperazin-1-yl]ethyl]thieno[3,4-d]pyrimidine-2,4-dione to produce methyl 3-[3-[2-[4-(4-fluorophenyl)piperazin-1-yl]ethyl]-2,4-dioxothieno[3,4-d]pyrimidin-1-yl]propanoate in 66% yield (11.9 g) after recrystallization from $CH_2Cl_2$/ether to afford a pale yellow solid, mp 165°–165.5° C.

Theor. $C_{22}H_{25}FN_4O_4S$: C,57.38;H,5.47;N,12.17. Found: C,57.36;H,5.47;N,12.09.

The above ester (11.43 g, 25 mmol) was hydrolyzed to its corresponding carboxylic acid as described in Example 1. There was obtained 9.77 g (88.2%) of 3-[3-[2-[4-(4-fluorophenyl)piperazin-1-yl]ethyl]-2,4-dioxothieno[3,4-d]pyrimidin-1-yl]propanoic acid as a cream-colored solid, mp 202°–203° C.

Theor. $C_{21}H_{23}FN_4O_4S \cdot \frac{1}{2}H_2O$: C,55.92;H,5.25;N,12.42. Found: C,55.67;H,5.20;N,12.23.

The above acid (8.42 g, 18.9 mmol) was cyclized to the title compound in 44.2% yield (3.60 g) after recrystallization from $CH_2Cl_2$/hexane to afford a yellow solid, mp 196°–197° C.

Theor. $C_{21}H_{21}FN_4O_3S$: C,58.86;H,4.94;N,13.08. Found: C,59.02;H,4.94;N,13.35.

EXAMPLE 10

3,4,5,7,8,9-Hexahydro-4-[3-[4-(2-methoxyphenyl)piperazin-1-yl]propyl]thieno[4,3,2-de]pyrido[1,2-c]pyrimidine-3,5,9-trione The title compound was produced following the procedure of Example 1 using 11.0 g (27.5 mmol) of 3-[3-[4-(2-methoxyphenyl)piperazin-1-yl]propyl]-thieno[3,4-d]-pyrimidine-2,4-dione to produce methyl 3-[3-[3-[4-(2-methoxyphenyl)piperazin-1-yl]propyl]-2,4-dioxothieno[3,4-d]pyrimidin-1-yl]propanoate in 87.4% yield (11.7 g). A portion of this material was converted to its tan hydrochloride salt using 2-propanol/HCl, mp 184°–192° C.

Theor. $C_{24}H_{30}N_4O_5S \cdot HCl \cdot H_2O$: C,53.27;H,6.15;N,10.36. Found: C,53.37;H,5.94;N,10.31.

The above ester (11.2 g, 23 mmol) was hydrolyzed to its corresponding carboxylic acid as described in Example 1. There was obtained 9.5 g (87.4%) of 3-[3-[3-[2-methoxyphenyl]piperazin-1-yl]propyl]-2,4-dioxothieno[3,4-d]pyrimidin-1-yl]propanoic acid as a light yellow solid. A portion of this material was crystallized from $CH_2Cl_2$/MeOH/$Et_2O$(1/0.1/1) to produce a white solid, mp 202°–203.5° C. (dec).

Theor. $C_{23}H_{28}N_4O_5S$: C,58.45;H,5.97;N,11.86. Found: C,58.16;H,5.91;N,11.74.

The above acid (7.8 g, 16.5 mmol) was cyclized as described in Example 1. There was obtained 4.7 g (62.7%) of the title compound which was recrystallized from $CH_2Cl_2$/ether to afford a light yellow solid, mp 163°–164° C.

Theor. $C_{23}H_{26}N_4O_4S$: C,60.77;H,5.77;N,12.33. Found: C,60.46;H,5.78;N,12.28.

EXAMPLE 11

3,4,5,7,8,9-Hexahydro-4-[4-[4-(2-methoxyphenyl)-piperazin-1-yl]butyl]thieno[4,3,2-de]pyrido[1,2-c]pyrimidine-3,5,9-trione To ice-cold toluene (120 mL) under nitrogen was added 12 mL (24 mmol) of a 2M $AlMe_3$/toluene solution followed by 4.35 g (24 mmol) of 4-[(2-methoxyphenyl)-piperazin-1-yl]butanamine (Y.-H. Wu et al., *J. Med Chem*, 12, 876 (1969)). After stirring for 10 minutes, 4.61 g (20 mmol) of methyl (4-ethoxycarbonylamino)-3-thiophenecarboxylate (prepared by the Schotten-Bauman reaction of methyl 4-aminothiophene-3-carboxylate hydrochloride and ethyl chloroformate) was added as a solution in toluene. This solution was warmed to reflux for 8 hours and then quenched with glacial AcOH. Concentrated $NH_4OH$ was added until the phases separated and the aqueous was extracted with $CH_2Cl_2$. The combined organic layers were washed with brine and dried ($MgSO_4$). Solvent removal produced a residue which was purified by flash silica gel chromatography using 2–4% MeOH in $CH_2Cl_2$. The desired product, 3-[4-[4-(2-methoxyphenyl)piperazin-1-yl]butyl]thieno[3,4-d]pyrimidine-2,4-dione was obtained as a creamed-colored solid in 19.7% yield (1.63 g) after recrystallization from chloroform/hexane, mp 162°–163.5° C.

Theor. $C_{21}H_{26}N_4O_3S$: C,60.84;H,6.32;N,13.52. Found: C,60.99;H,6.29;N,13.40.

The above compound (5.6 g, 13.5 mmol) was mixed with methyl acrylate as described in Example 1 to produce 4.0 g (59.1%) of methyl 3-[3-[4-[4-(2-methoxyphenyl)piperazin-1-yl]butyl]-2,4-dioxothieno[3,4-d]pyrimidin-1-yl]propanoate.

The above crude ester was hydrolyzed to its corresponding carboxylic acid as described in Example 1. There was obtained 3.75 g (96.4%) of 3-[3-[4-[4-(2-methoxyphenyl]piperazin-1-yl]butyl]-2,4-dioxothieno[3,4-d]pyrimidin-1-yl]propanoic acid as a gold-colored foam.

The above crude acid was cyclized as described in Example 1. There was obtained 639 mg (17.7%) of the title compound after recrystallization from $CH_2Cl_2$/hexane to afford a tan solid, mp 136.5°–138° C.

Theor. $C_{24}H_{28}N_4O_4S$: C,61.52;H,6.02;N,11.96. Found: C,61.45;H,5.99;N,12.12.

EXAMPLE 12

3,4,5,7,8,9-Hexahydro-4-[5-[4-(2-methoxyphenyl)piperazin-1-yl]pentyl]thieno[4,3,2-de]pyrido[1,2-c]pyrimidine-3,5,9-trione Methyl 4-aminothiophene-3-carboxylate was reacted with one equivalent of 5-bromopentylisocyanate in toluene at room temperature for 4 hours to produce N-(5-bromopentyl)-N'-(4-carbomethoxythien-3-yl)urea as a tan solid (98%). This material was recrystallized from $CH_2Cl_2$/ether/hexane to afford the urea as a white solid, mp 92°–93.5° C.

Theor. $C_{12}H_{17}BrN_2O_3S$: C,41.26;H,4.91;N,8.02. Found: C,41.52;H,4.94;N,7.98.

The above urea (8.0 g, 23 mmol) was reacted with 1-(2-methoxyphenyl)piperazine hydrochloride (10.48 g, 45 mmol), NaI (1.72 g, 11 mmol) and $NaHCO_3$ (7.69 g, 92 mmol) in 50 mL of 2-propanol at reflux for 6 hours under a nitrogen blanket. After cooling, water was added and the 2-propanol was removed by distillation. The brown residue was dissolved in $CH_2Cl_2$ and washed with water and brine and dried (MgSO$_4$). After the solvent has been removed in vacuo, the tan residue was dissolved in MeOH and treated with 1.1 equivalents of 50% NaOH and the solution was refluxed for 3.5 hours. The pH of the solution was adjusted to 6 with 2N HCL and the methanol was removed by distillation. The resulting oil was dissolved in CH$_2$Cl$_2$ and washed with water and brine and dried (MgSO$_4$). Solvent removal produced 10.81 g (91%) of 3-[5-[4-(2-methoxyphenyl)piperazin-1-yl]pentyl]thieno[3,4-d]pyrimidine-2,4-dione which was crystallized from CH$_2$Cl$_2$/ether to afford a tan solid, mp 148°–153° C.

Theor. C$_{22}$H$_{28}$N$_4$O$_3$S: C,61.66;H,6.59;N,13.08. Found: C,61.41;H,6.61;N,13.21.

The title compound was produced following the procedure of Example 1 using 9.91 g (23 mmol) of 3-[5-[4-(2-methoxyphenyl)piperazin-1-yl]pentyl]thieno[3,4-d]-pyrimidine-2,4-dione in DMF for several days to produce methyl 3-[3-[5-[4-(2-methoxyphenyl)piperazin-1-yl]pentyl]-2,4-dioxothieno[3,4-d]pyrimidin-1-yl]propanoate in 23% yield (2.8 g). A portion of this material was converted to its brown hydrochloride salt using 2-propanol/HCl.

Theor. C$_{26}$H$_{34}$N$_4$O$_5$S.HCl.3/4H$_2$O.1/3isopropanol: C,55.04;H,6.78;N,9.51. Found: C,55.34;H,6.68;N,9.85.

The above ester (3.12 g, 6 mmol) was hydrolyzed to its corresponding carboxylic acid as described in Example 1. There was obtained 2.15 g (71%) of 3-[3-[5-[2-methoxyphenyl)piperazin-1-yl]pentyl]-2,4-dioxothieno[3,4-d]pyrimidin-1-yl]propanoic acid as a tan solid.

The above acid (2.15 g, 4 mmol) was cyclized as described in Example 1. There was obtained 0.34 g (16%) of the title compound which was recrystallized from CH$_2$Cl$_2$/ether to afford a tan solid, mp 168°–170° C.

Theor. C$_{25}$H$_{30}$N$_4$O$_4$S.¼H$_2$O: C,61.64;H,6.31;N,11.50. Found: C,61.76;H,6.34;N,11.49.

EXAMPLE 13

3,4,5,7,8,9-Hexahydro-2-methyl-4-[2-[4-(2-methoxyphenyl)piperazin-1-yl]ethyl]thieno[4,3,2-de]pyrido[1,2-c]pyrimidine-3,5,9-trione The title compound was produced following the procedure of Example 1 using 16.02 g (40 mmol) of 3-[2-[4-(2-methoxyphenyl)piperazin-1-yl]ethyl]-5-methylthieno[3,4-d]pyrimidine-2,4-dione to produce methyl 3-[3-[2-[4-(2-methoxyphenyl)piperazin-1-yl]ethyl]-5-methyl-2,4-dioxothieno[3,4-d]pyrimidin-1-yl]propanoate in 90.2% yield (17.56 g) after recrystallization from CH$_2$Cl$_2$/hexane to afford a tan solid, mp 127°–128° C.

Theor. C$_{24}$H$_{30}$N$_4$O$_5$S: C,59.24;H,6.21;N,11.52. Found: C,59.14;H,6.25;N,11.54.

The above ester (12.56 g, 26.6 mmol) was hydrolyzed to its corresponding carboxylic acid sodium salt as described in Example 1. There was obtained 11.66 g (95.6%) of 3-[3-[2-[4-(2-methoxyphenyl)piperazin-1-yl]ethyl]-5-methyl-2,4-dioxothieno[3,4-d]pyrimidin-1-yl]propanoic acid sodium salt as a white solid, mp 218°–224° C. (dec).

Theor. C$_{23}$H$_{27}$N$_4$NaO$_5$S: C,55.86;H,5.50;N,11.32. Found: C,55.52;H,5.72;N,11.27.

The above acid sodium salt (8.21 g, 17.4 mmol) was cyclized as described in Example 1. There was obtained 6.58 g (83.2%) of the title compound after recrystallization from CH$_2$Cl$_2$/hexane as a gold-colored solid, mp 173°–174° C.

Theor. C$_{23}$H$_{26}$N$_4$O$_4$S: C,60.77;H,5.77;N,12.33. Found: C,60.47;H,5.86;N,12.33.

EXAMPLE 14

7,8-Dihydro-4-[2-[4-(2-methoxyphenyl)-piperazin-1-yl]ethyl]thieno[2,3,4-de]pyrido[1,2-c]pyrimidine-3,5,9-trione The title compound was produced following the procedure of Example 1 using 12.46 g (32.2 mmol) of 3-[2-[4-(2-methoxyphenyl)piperazin-1-yl]ethyl]-thieno[3,2-d]pyrimidine-2,4-dione to produce methyl 3-[3-[2-[4-(2-methoxyphenyl)piperazin-1-yl]ethyl]-2,4-dioxothieno[3,2-d]pyrimidin-1-yl]propanoate in 83% yield (12.63 g) after recrystallization from CH$_2$Cl$_2$/hexane to afford a white solid, mp 151°–152° C.

Theor. C$_{23}$H$_{28}$N$_4$O$_5$S: C,58.45;H,5.97;N,11.86. Found: C,58.22;H,5.91;N,11.90.

The above ester (10.57 g, 22.4 mmol) was hydrolyzed to its corresponding carboxylic acid as described in Example 1. There was obtained 9.35 g (91.2%) of 3-[3-[2-[4-(2-methoxyphenyl)piperazin-1-yl]ethyl]-2,4-dioxothieno[3,2-d]pyrimidin-1-yl]propanoic acid as an off-white solid, mp 215°–216° C.

Theor. C$_{22}$H$_{26}$N$_4$O$_5$S.½H$_2$O: C,56.52;H,5.82;N,11.98. Found: C,56.52;H,5.75;N,12.03.

The above acid (5.61 g, 12.2 mmol) was cyclized as described in Example 1. There was obtained 1.84 g (34.1%) of the title compound after recrystallization from CH$_2$Cl$_2$/ether to afford a peach-colored solid, mp 160°–162° C.

Theor. C$_{22}$H$_{24}$N$_4$O$_4$S: C,59.98;H,5.49;N,12.72. Found: C,59.95;H,5.53;N,12.78.

EXAMPLE 15

4,7,8,9-Tetrahydro-4-[2-[4-(2-methoxyphenyl)-piperazin-1-yl]ethyl]thieno[4,3,2-de]pyrimido[3,4-a]azepine-3,5,10-trione The title compound was produced from the known ester, ethyl 4-[2-[4-(2-methoxyphenyl)piperazin-1-yl]ethyl]-2,4-dioxothieno[3,4-d]pyrimidin-1-yl]butanoate (J. Press and R. Russell, U.S. Pat. No. 4,670,560). This ester (8.03 g, 16 mmol) was hydrolyzed to its corresponding carboxylic acid as described in Example 1. There was obtained 5.34 g (70.6%) of 4-[3-[2-[4-(2-methoxyphenyl)piperazin-1-yl]ethyl]-2,4-dioxothieno[3,4-d]pyrimidin-1-yl]butanoic acid as a pale yellow solid.

The above crude acid (4.64 g, 9.8 mmol) was cyclized as described in Example 1. There was obtained 3.13 g (70.1%) of the title compound after recrystallization from CH$_2$Cl$_2$/hexane to afford a white solid, mp 171°–173° C.

Theor. C$_{23}$H$_{26}$N$_4$O$_4$S: C,60.77;H,5.77;N,12.33. Found: C,60.39;H,5.77;N.12.35.

EXAMPLE 16

4,7,8,9,10,11-Hexahydro-4-[2-[4-(2-methoxyphenyl)piperazin-1-yl]ethyl]thieno[4,3,2-de]pyrimido[3,4-a]azocine-3,5,11-trione The title compound was prepared by first alkylating 10.67 g (27.6 mmol) of 3-[2-[4-(2-methoxyphenyl)piperazin-1-yl]ethyl]thieno[3,4-d]pyrimidine-2,4-dione with 7.5 g (36 mmol) of ethyl bromopentanoate in DMF/NaH as described in the literature (J. Press and R. Russell, U.S. Pat. No. 4,670,560). The ester, ethyl 5-[3-[2-[4-(2-methoxyphenyl)piperazin-1-yl]ethyl]-2,4-dioxothieno[3,4-d]pyrimidin-1-yl]pentanoate, was obtained in 88% yield (12.61 g) after chromatography. A portion of this material was recrystallized from CH₂Cl₂/hexane to afford a yellow solid, mp 108°-110° C.

Theor. $C_{26}H_{34}N_4O_5S$: C,60.68;H,6.68;N,10.89. Found: C,60.79;H,6.65;N,10.74.

The above ester (10.12 g, 20 mmol) was hydrolyzed to its corresponding carboxylic acid as described in Example 1. There was obtained after recrystallization from EtOH, 5.92 g (62.1%) of 5-[3-[2-[4-(2-methoxyphenyl)piperazin-1-yl]ethyl]-2,4-dioxothieno[3,4-d]pyrimidin-1-yl]pentanoic acid as a light yellow solid, mp 211°-213° C.

Theor. $C_{24}H_{30}N_4O_5S$: C,59.24;H,6.21;N,11.52. Found: C,59.13;H,6.19;N,11.49.

The above acid (5.20 g, 10.7 mmol) was cyclized as described in Example 1. There was obtained 3.65 g (72.9%) of the title compound after recrystallization from ether to afford a cream-colored solid, mp 162.5°-164° C.

Theor. $C_{24}H_{28}N_4O_4S$: C,61.52;H,6.02;N,11.96. Found: C,61.14;H,6.10;N,11.55.

EXAMPLE 17

3,4,5,7,8,9-Hexahydro-4-[2-(4-phenyl-1,2,3,6-tetrahydropyridin-1-yl)ethyl]thieno[4,3,2-de]pyrido[1,2-c]pyrimidine-3,5,9-trione The title compound was prepared by starting with 3-[2-(4-phenyl-1,2,3,6-tetrahydropyridin-1-yl)ethyl]-thieno[3,4-d]pyrimidine-2,4-dione. This starting material was prepared by the procedure in Example 6 using 7.47 g (38.2 mmol) of 4-phenyl-1,2,3,6-tetrahydropyridine hydrochloride and 5.0 g (19 mmol) of the urea in 50.6% yield (3.41 g) after recrystallization from methanol/chloroform/ether to give a tan solid, mp 209°-213° C. (dec).

Theor. $C_{19}H_{19}N_3O_2S$: C,64.56;H,5.42;N,11.89. Found: C,64.11;H,5.33;N,11.86.

The above compound (9.32 g, 24.2 mmol) was reacted with methyl acrylate as described in Example 1 to produce methyl 3-[3-[2-(4-phenyl-1,2,3,6-tetrahydropyridin-1-yl)ethyl]-2,4-dioxothieno[3,4-d]pyrimidin-1-yl]propanoate in 82.4% yield (9.4 g) after chromatography.

The above crude ester (7.67 g, 16.3 mmol) was hydrolyzed to its corresponding carboxylic acid as described in Example 1. There was obtained 5.84 g (78.5%) of 3-[3-[2-(4-phenyl-1,2,3,6-tetrahydropyridin-1-yl)ethyl]-2,4-dioxothieno[3,4-d]pyrimidin-1-yl]propanoic acid.

The above crude acid was cyclized as in Example 1. There was obtained 2.27 g (40.6%) of the title compound after recrystallization from CH₂Cl₂/hexane to afford a tan solid, mp 158°-160° C. (dec).

Theor. $C_{22}H_{21}N_3O_3S$: C,64.85;H,5.19;N,10.31. Found: C,64.70;H,5.33;N,10.23.

EXAMPLE 18

4-[4-[4-(3-Trifluoromethylphenyl)piperazin-1-yl]butyl]-3,4,5,7,8,9-hexahydrothieno[4,3,2-de]-pyrido[1,2-c]pyrimidine-3,5,9-trione Methyl 4-aminothiophene-3-carboxylate was reacted with one equivalent of 4-bromobutylisocyanate in toluene at room temperature for 12 hours to produce N-(4-bromobutyl)-N'-(4-carbomethoxythien-3-yl] urea as a tan solid, mp 85°-86° C.

The above urea (12.41 g, 37.5 mmol) was reacted with 1-(3-trifluoromethylphenyl)piperazine hydrochloride (15 g, 56.2 mmol) as described in Example 12 to produce 5.8 g (34%) of the known 3-[4-[4-(3-trifluoromethylphenyl)piperazin-1-yl]butyl]thieno[3,4-d]pyrimidine-2,4-dione (J. Press and R. Russell, U.S. Pat. No. 4,670,560) after recrystallization from CH₂Cl₂/hexane as a white solid, mp 126°-128° C.

Theor. $C_{21}H_{23}F_3N_4O_2S$: C,55.74;H,5.12;N,12.38. Found: C,55.78;H,5.16;N,12.35.

The title compound was produced following the procedure of Example 1 using 4.28 g (9.5 mmol) of 3-[4-[4-(3-trifluoromethylphenyl)piperazin-1-yl]butyl]-thieno[3,4-d]pyrimidine-2,4-dione in DMF at 45° C. for 16 hours to produce methyl 3-[3-[4-[4-(3-trifluoromethylpheny)piperazin-1-yl]butyl]-2,4-dioxothieno[3,4-d]pyrimidin-1-yl]propanoate in 80.5% yield (4.1 g).

The above crude ester (3.1 g, 5.8 mmol) was hydrolyzed to its corresponding carboxylic acid as described in Example 1. There was obtained 2.96 g (98%) of 3-[3-[4-(3-trifluoromethylphenyl)piperazin-1-yl]butyl]-2,4-dioxothieno[3,4-d]pyrimidin-1-yl]propanoic acid as a white solid.

The above acid (2.42 g, 4.5 mmol) was cyclized as described in Example 1. There was obtained 1.05 g (45%) of the title compound after recrystallization from CH₂Cl₂/hexane as a light yellow solid, mp 163°-164° C.

Theor. $C_{24}H_{25}F_3N_4O_3S$: C,56.91;H,4.97;N,11.06. Found: C,56.63;H,4.76;N,11.12.

EXAMPLE 19

4-[2-[4-(4-Fluorobenzoyl)piperidin-1-yl]ethyl]-3,4,5,7,8,9-hexahydrothieno[4,3,2-de]pyrido[1,2-c]pyrimidine-3,5,9-trione The title compound was prepared by starting with 3-[2-[4-(4-fluorobenzoyl)piperidin-1-yl]ethyl]thieno[3,4-d]pyrimidine-2,4-dione. This material (9.0 g, 22.4 mmol) was reacted with methyl acrylate as described in Example 1 to produce 6.54 g (59.8%) of methyl 3-[3-[2-[4-(4-fluorobenzoyl)piperidin-1-yl]ethyl]-2,4-dioxothieno[3,4-d]pyrimidin-1-yl]propanoate as an orange oil after chromatography. A portion of this material was crystallized from CH₂Cl₂/hexane to afford a peach-colored solid, mp 122°-123° C.

Theor. $C_{24}H_{26}FN_3O_5S$: C,59.12;H,5.38;N,8.62. Found: C,59.18;H,5.42;N,8.67.

The above ester (5.0 g, 10.3 mmol) was hydrolyzed to its corresponding carboxylic acid as described in Example 1. There was obtained 3.81 g (78.5%) of 3-[3-[2-[4-(4-fluorobenzoyl)piperidin-1-yl]ethyl]-2,4-dioxothieno[3,4-d]pyrimidin-1-yl]propanoic acid.

The above crude acid (3.8 g, 8 mmol) was cyclized as in Example 1. There was obtained 1.8 g (49.4%) of the title compound after recrystallization from CH₂Cl₂/hexane to afford a pale-yellow solid, mp 218°-219° C.

Theor. $C_{23}H_{22}FN_3O_4S$: C,60.65;H,4.87;N,9.22. Found: C,60.72;H,4.80;N,9.04.

EXAMPLE 20

4-[2-[4-[Bis(4-fluorophenyl)methylene]piperidin-1-yl]ethyl]-3,4,5,7,8,9-hexahydrothieno[4,3,2-de]pyrimidine-3,5,9-trione The title compound was prepared by starting with 3-[2-[4-(bis(4-fluorophenyl)methylene]piperidin-1-yl]e- thyl]thieno[3,4-d]pyrimidine-2,4-dione. This material (7.48 g, 16 mmol) was reacted with methyl acrylate as described in Example 1 to produce 5.48 g (62%) of methyl 3-[3-[2-[4-[bis(4-fluorophenyl)methylene]piperidin-1-yl]ethyl]-2,4-dioxothieno[3,4-d]pyrimidin-1-yl]propanoate as a cream-colored solid after recrystallization from $CH_2Cl_2$/ether/hexane, mp 111°–114° C.

Theor. $C_{30}H_{29}F_2N_3O_4S$: C,63.70;H,5.17;N,7.43. Found: C,63.57;H,5.13;N,7.28.

The above ester (5.18 g, 9.2 mmol) was hydrolyzed to its corresponding carboxylic acid as described in Example 1. There was obtained 4.64 g (92%) of 3-[3-[2-[4-[bis(4-fluorophenyl)methylene]piperidin-1-yl]ethyl]-2,4-dioxothieno[3,4-d]pyrimidin-1-yl]propanoic acid.

The above crude acid (4.02 g, 7 mmol) was cyclized as in Example 1. There was obtained 1.43 g (37%) of the title compound after recrystallization from $CH_2Cl_2$/hexane/ether as a light-yellow solid, mp 221°–224° C.

Theor. $C_{29}H_{25}F_2N_3O_3S$: C,65.27;H,4.72;N,7.88. Found: C,64.82;H,4.79;N,7.63.

EXAMPLE 21

3,4,5,7,8,9-Hexahydro-9-hydroxy-4-[2-[4-(2-methoxyphenyl)piperazin-1-yl]ethyl]thieno[4,3,2-de]pyrido[1,2-c]pyrimidine-3,5-dione The trione (2.71 g, 6.15 mmol) from Example 1 was mixed with 233 mg (6.15 mmol) of sodium borohydride in absolute ethanol. After stirring at room temperature for 3 days, water was added and the ethanol was removed in vacuo. The pH of the aqueous solution was adjusted to 12 with 2N NaOH and then the aqueous solution was extracted with $CH_2Cl_2$. The combined extracts were washed with brine and dried ($MgSO_4$). Solvent removal produced a residue which was crystallized from chloroform/ethanol/ether to afford 1.58 g (58%) of the title compound as a light-yellow solid, mp 210°–211.5° C.

Theor. $C_{22}H_{26}N_4O_4S$: C,59.71;H,5.92;N,12.66. Found: C,59.69;H,5.86;N,12.59.

EXAMPLE 22

10-Hydroxy-4,7,8,9-tetrahydro-4-[2-[4-(2-methoxyphenyl)piperazin-1-yl]ethyl]thieno[4,3,2-de]-pyrimido[3,4-a]azepine-3,5-dione The trione (5.68 g, 12.5 mmol) from Example 15 was mixed with 473 mg (12.5 mmol) of sodium borohydride as described in Example 21 except the stirring time was 24 hours. There was obtained 5.25 g (92%) of the title compound as a white solid after trituration with ether. A portion of this material was recrystallized from $CH_2Cl_2$/hexane, mp 148°–149.5° C.

Theor. $C_{23}H_{28}N_4O_4S$: C,60.50;H,6.18;N,12.27. Found: C,60.36;H,6.15;N,12.24.

EXAMPLE 23

3,4,5,7,8,9-Hexahydro-9-hydroxy-4-[2-[4-(2-methoxyphenyl)piperazin-1-yl]ethyl]-2-methyl-thieno[4,3,2-de]-pyrido[1,2-c]pyrimidine-3,5-dione The trione (3.5 g, 7.7 mmol) from Example 13 was mixed with 291 mg (7.7 mmol) of sodium borohydride as described in Example 21. There was obtained 3.36 g (95.6%) of the title compound as a cream-colored solid after trituration from hexane, mp 150° C. (softens), 162°–164° C.

Theor. $C_{23}H_{28}N_4O_4S$: C,60.50;H,6.18;N,12.27. Found: C,60.24;H,6.19;N,12.38.

EXAMPLE 24

3,4,5,7-Tetrahydro-4-[2-[4-(2-methoxyphenyl)piperazin-1-yl]ethyl]thieno[4,3,2-de]pyrido[1,2-c]pyrimidine-3,5-dione The alcohol (2.72 g, 6.1 mmol) from Example 21 was suspended in ice-cold $CH_2Cl_2$ and was treated with 0.774 g (6.8 mmol) of methanesulfonyl chloride followed by one equivalent of triethylamine. After refluxing for 16 hours, the reaction was quenched with water and the organic layer was washed with saturated $NaHCO_3$ solution and brine and dried ($MgSO_4$). Solvent removal produced a residue which was purified by flash silica gel chromatography using 2% MeOH in $CH_2Cl_2$. There was obtained 1.30 g (50.2%) of the title compound as a yellow solid after recrystallization from $CH_2Cl_2$/ether, mp 180°–181° C.

Theor. $C_{22}H_{24}N_4O_3S$: C,62.24;H,5.70;N,13.20. Found: C,61.86;H,5.73;N,13.04.

EXAMPLE 25

3,4,5,7,9,10-Hexahydro-4-[2-[4-(2-methoxyphenyl)piperazin-1-yl]ethyl]-9H-thieno[4,3,2-de]pyrimido[1,2-a]1,4]diazepine-3,5,10-trione The trione (2.5 g, 5.7 mmol) from Example 1 was mixed with 790 mg (11.35 mmol) of hydroxylamine hydrochloride and sodium acetate in absolute ethanol at reflux for 16 hours. After water had been added, the ethanol was removed in vacuo and the solid isolated and dried.

The above crude oxime was dissolved in Eaton's reagent and warmed to 100° C. under nitrogen for 2 hours. After this red solution had been carefully poured into the ice-water, the pH of the solution was carefully adjusted to 8 with concentrated $NH_4OH$ at 40°–45° C. The solid was isolated and purified by flash silica gel chromatography using 1–4% MeOH in $CH_2Cl_2$. The material obtained from the column was recrystallized from $CH_2Cl_2$/ether to produce 472 mg (18.2%) of the title compound as a yellow crystalline solid, mp 197°–199° C.

Theor. $C_{22}H_{25}N_5O_4S$: C,58.00;H,5.53;N,15.38. Found: C,57.98;H,5.55;N,15.19.

EXAMPLE 26

3,4,5,7,8,9-Hexahydro-9-methoxyimino-4-[2-[4-(2-methoxyphenyl)piperazin-1-yl]ethyl]-thieno[4,3,2-de]-pyrido[1,2-c]pyrimidine-3,5-dione The trione (7.0 g, 15.9 mmol) from Example 1 was mixed with 2.66 g (31.8 mmol) of O-methylhydroxylamine hydrochloride and 2.6 g (31.8 mmol) of sodium acetate in 160 mL of absolute ethanol. After this mixture had been refluxed under nitrogen for 16 hours the solvent was removed in vacuo. Aqueous sodium bicarbonate was added, the aqueous solution was extracted with $CH_2Cl_2$ and the combined extracts were washed with brine and dried ($Na_2SO_4$). Solvent removal produced 8.4 g of yellow solid which was crystallized from $CH_2Cl_2$/ether/hexane (2/2/1) to afford 5.5 g (73.7%) of the title compound as a yellow solid, mp 165°–168° C.

Theor. $C_{23}H_{27}N_5O_4S$: C,58.83;H,5.80;N,14.92. Found: C,58.94;H,5.90; N,14.75.

EXAMPLE 27

4,7,8,9-Tetrahydro-10-methoxyimino-4-[2-[4-(2-methoxyphenyl)piperazin-1-yl]ethyl]thieno[4,3,2-de]-pyrimido[3,4-a]azepine-3,5-dione The title compound was prepared by the procedure in Example 26 starting with 930 mg (2 mmol) of the trione from Example 15 and 854 mg (10 mmol) of O-methylhydroxylamine hydrochloride. There was obtained 825 mg (85.3%) of the title compound as a white solid after recrystallization from $CH_2Cl_2$/hexane, mp 185.5°–187° C.

Theor. $C_{24}H_{29}N_5O_4S$: C,59.61;H,6.04;N,14.48. Found: C,59.63;H,5.98;N,14.47.

EXAMPLE 28

3,4,5,7,8,9-Hexahydro-9-methoxyimino-4-[2-[4-(2-methoxyphenyl)piperazin-1-yl]ethyl]-2-methyl-thieno[4,3,2-de]pyrido[1,2-c]pyrimidine-3,5-dione The title compound was prepared by the procedure in Example 26 starting with 1.0 g (2.2 mmol) of the trione from Example 13 and 367 mg (4.4 mmol) of O-methylhydroxylamine hydrochloride. There was obtained 604 mg (56.8%) of the title compound as a white cottony solid after recrystallization from $CH_2Cl_2$/hexane, mp 152°–153° C.

Theor. $C_{24}H_{29}N_5O_4S$: C,59.61;H,6.04;N,14.48. Found: C,59.44;H,6.01;N,14.32.

EXAMPLE 29

3,4,5,7,8,9-Hexahydro-9-methoxyimino-4-[3-[4-(2-methoxyphenyl)piperazin-1-yl]propyl]thieno-[4,3,2-de]-pyrido[1,2-c]pyrimidine-3,5-dione The title compound was prepared by the procedure in Example 26 starting with 2.0 g (4.4 mmol) of the trione from Example 10 and 735 mg (8.8 mmol) of O-methylhydroxylamine hydrochloride. There was obtained 400 mg (18.8%) of the title compound after chromatography which was recrystallized from $CH_2Cl_2$/ether to afford a tan solid, mp 164°–166.5° C.

Theor. $C_{24}H_{29}N_5O_4S$: C,59.61;H,6.04;N,14.48. Found: C,59.41;H,6.09;N,14.46.

EXAMPLE 30

9-Acetyloxy-3,4,5,7,8,9-hexahydro-4-[2-[4-(2-methoxyphenyl)piperazin-1-yl]ethyl]thieno[4,3,2-de]pyrido[1,2-c]pyrimidine-3,5-dione The alcohol (2.0 g, 4.5 mmol) from Example 21 was suspended in ice-cold $CH_2Cl_2$ and treated with 1.5 equivalents of 4-dimethylaminopyridine and 390 mg (4.97 mmol) of acetyl chloride. After this mixture had been stirred at reflux for 16 hours, the golden-brown solution was washed with water and brine and dried ($MgSO_4$). Solvent removal produced a residue which was purified by flash silica gel chromatography using 2% MeOH in $CH_2Cl_2$. There was obtained 1.13 g (52%) of the title compound as a yellow solid after recrystallization from ether, mp 120°–122° C.

Theor. $C_{24}H_{28}N_4O_5S$: C,59.48;H,5.82;N,11.56. Found: C,59.87;H,5.83;N,11.89.

EXAMPLE 31

3,4,5,7,8,9-Hexahydro-4[4-(2-methoxyphenyl)piperazin-1-yl]-ethyl]-9-(butanoyloxy)thieno[4,3,2-de]-pyrido[1,2-c]pyrimidine-3,5-dione The title compound was produced by the procedure in Example 30 using 1.5 g (3.4 mmol) of the alcohol from Example 21 and 397 mg (3.7 mmol) of butanoyl chloride. There was obtained 552 mg (31.7%) of the title compound as a beige solid after recrystallization from ether/hexane, mp 117° C. (softens), 121°–122° C.

Theor. $C_{26}H_{32}N_4O_5S$: C,60.92;H,6.29;N,10.93. Found: C,60.59;H,6.38;N,10.88.

EXAMPLE 32

3,4,5,7,8,9-Hexahydro-4-[2-[4-(2-methoxyphenyl)piperazin-1-yl]ethyl]-9-(hexanoyloxy)thieno[4,3,2-de]-pyrido[1,2-c]pyrimidine-3,5-dione The title compound was produced by the procedure in Example 30 using 1.5 g (3.4 mmol) of the alcohol from Example 21 and 500 mg (3.7 mmol) of hexanoyl chloride. There was obtained 573 mg (31.2%) of the title compound as a yellow solid after recrystallization from ether/hexane, mp 99°–100° C.

Theor. $C_{28}H_{36}N_4O_5S$: C,62.20;H,6.71;N,10.36. Found: C,62.32;H,6.79;N,10.39.

EXAMPLE 33

3,4,5,7,8,9-Hexahydro-9-(2-methylpropanoyloxy)-4-[2-[4-(2-methoxyphenyl)piperazin-1-yl]ethyl]thieno[4,3,2-de]pyrido[1,2-c]pyrimidine-3,5-dione The title compound was produced by the procedure in Example 30 using 2.0 g (4.5 mmol) of the alcohol from Example 21 and 530 mg (5.0 mmol) of isobutanoyl chloride. There was obtained 1.59 g (68.5%) of the title compound as a white solid after recrystallization from $CH_2Cl_2$/ether, mp 166°–167° C.

Theor. $C_{26}H_{32}N_4O_5S$: C,60.92;H,6.29;N,10.93. Found: C,60.71;H,6.25;N,10.70.

EXAMPLE 34

3,4,5,7,8,9-Hexahydro-4-[2-[4-(2-methoxyphenyl)piperazin-1-yl]ethyl]-9-[(2,2-dimethyl)propanoyloxy]-thieno[4,3,2-de]pyrido[1,2-c]pyrimidine-3,5-dione The title compound was produced by the procedure in Example 30 using 1.5 g (3.4 mmol) of the alcohol from Example 21 and 450 mg (3.7 mmol) of trimethylacetyl chloride. There was obtained 1.3 g (72.7%) of the title compound as a white solid after recrystallization from hexane, mp 185.5°–187° C.

Theor. $C_{27}H_{34}N_4O_5S$: C,61.57;H,6.51;N,10.64. Found: C,61.86;H,6.59;N,10.61.

EXAMPLE 35

9-Benzoyloxy-3,4,5,7,8,9-hexahydro-4-[2-[4-(2-methoxyphenyl)piperazin-1-yl]ethyl]thieno[4,3,2-de]-pyrido[1,2-c]pyrimidine-3,5-dione The title compound was produced by the procedure in Example 30 using 2.0 mg (4.5 mmol) of the alcohol from Example 21 and 699 mg (4.97 mmol) of benzoyl chloride. There was obtained 1.14 (46.4%) of the title compound as a yellow solid after recrystallization from $CH_2Cl_2$/hexane, mp 174°–176° C.

Theor. $C_{29}H_{30}N_4O_5S$: C,63.72;H,5.53;N,10.25. Found: C,63.85;H,5.47;N,10.03.

EXAMPLE 36

3,4,5,7,8,9-Hexahydro-9-(4-methoxy)benzoyloxy-4-[2-[4-(2-methoxyphenyl)piperazin-1-yl]ethyl]thieno[4,3,2-de]pyrido[1,2-c]pyrimidine-3,5-dione The title compound was produced by the procedure in Example 30 using 1.5 g (3.4 mmol) of the alcohol from Example 21 and 636 mg (3.7 mmol) of 4-methoxybenzoyl chloride. There was obtained 1.15 (58.7%) of the title compound as a white solid after trituration with hexane, mp 110° C. (softens), 120°-122° C.

Theor. $C_{30}H_{32}N_4O_6S$: C,62.48;H,5.59;N,9.72. Found: C,62.15;H,5.63;N,9.70.

EXAMPLE 37

9-(4-Chlorobenzoyloxy)-3,4,5,7,8,9-hexahydro-4-[2-[4-(2-methoxyphenyl)piperazin-1-yl]ethyl]thieno[4,3,2-de]pyrido[1,2-c]pyrimidine-3,5-dione The title compound was produced by the procedure in Example 30 using 1.5 g (3.4 mmol) of the alcohol from Example 21 and 653 mg (3.7 mmol) of 4-chlorobenzoyl chloride. There was obtained 1.55 g (78%) of the title compound as a white solid after trituration from hexane, mp 124° C. (softens), 128°-130° C.

Theor. $C_{29}H_{29}ClN_4O_5S$: C,59.94;H,5.03;N,9.64. Found: C,59.85;H,5.05;N,9.62.

EXAMPLE 38

9-Amino-3,4,5,7,8,9-hexahydro-4-[2-[4-(2-methoxyphenyl)piperazin-1-yl]ethyl]thieno[4,3,2-de]pyrido[1,2-c]pyrimidine-3,5-dione The oxime (1.4 g, 2.99 mmol) from Example 26 was slurried in 20 mL of ice-cold THF under nitrogen and treated with 12 mL of 1M $BH_3$/THF. After refluxing the solution for two hours, the reaction was carefully quenched with 2N HCl and the THF was removed in vacuo. The resulting acidic residue was warmed on a steambath for 15-20 minutes, cooled and then the pH was adjusted to 10 with 2N NaOH. The aqueous solution was extracted with $CH_2Cl_2$ and the combined extracts were washed with brine and dried ($Na_2SO_4$). Solvent removal produced 1.3 g (98%) of the title compound which was crystallized from $CH_2Cl_2$/ether to afford a beige solid, mp 152°-155° C.

Theor. $C_{22}H_{27}N_5O_3S$: C,59.84;H,6.16;N,15.86. Found: C,59.42;H,6.12;N,16.08.

EXAMPLE 39

9-Acetylamino-3,4,5,7,8,9-hexahydro-4-[2-[4-(2-methoxyphenyl)piperazin-1-yl]ethyl]thieno[4,3,2-de]pyrido[1,2-c]pyrimidine-3,5-dione The amino compound (883 mg, 2 mmol) from Example 38 in 20 mL of ice-cold $CH_2Cl_2$ was treated with 0.31 mL (2.2 mmol) of triethylamine, 61 mg (0.5 mmol) of 4-dimethylaminopyridine and a 3 mL $CH_2Cl_2$ solution of acetyl chloride (0.16 mL, 2.2 mmol). After the mixture had warmed to room temperature, it was quenched with water and the organic layer was removed and dried (MgSO$_4$). Solvent removal produced a yellow foam which was crystallized from $CH_2Cl_2$/ether to afford 0.65 g (67.2%) of the title compound as a yellow solid, mp 193.5°-196.5° C.

Theor. $C_{24}H_{29}N_5O_4S$: C,59.61;H,6.04;N,14.48. Found: C,59.43;H,6.16;N,14.41.

EXAMPLE 40

9-Benzoylamino-3,4,5,7,8,9-hexahydro-4-[2-[4-(2-methoxyphenyl)piperazin-1-yl]ethyl]thieno[4,3,2-de]pyrido[1,2-c]pyrimidine-3,5-dione The title compound was produced by the procedure in Example 39 using 0.7 g (1.59 mmol) of the amine from Example 38. There was obtained 0.57 g (65.7%) of the title compound as a beige solid after recrystallization from $CH_2Cl_2$/ether, mp 202°-203° C.

Theor. $C_{29}H_{31}N_5O_4S$: C,63.83;H,5.73;N,12.84. Found: C,63.85;H,5.86;N,12.82.

EXAMPLE 41

4-[2-[4-(3-Chlorophenyl)piperazin-1-yl]ethyl]-3,4,5,7,8,9-hexahydro-9-methoxyiminothieno[4,3,2-de]pyrido[1,2-c]pyrimidine-3,5-dione The title compound was prepared by the procedure in Example 26 starting with 1.07 g (2.3 mmol) of the trione from Example 7 and 386 mg (4.6 mmol) of O-methylhydroxylamine hydrochloride. There was obtained 680 mg (62%) of the title compound as a white solid after recrystallization from $CH_2Cl_2$/hexane, mp 182.5°-183.5° C.

Theor. $C_{22}H_{24}ClN_5O_3S$: C,55.75;H,5.10;N,14.78. Found: C,55.61;H,5.08;N,14.83.

EXAMPLE 42

4-[4-[4-(4-Fluorobenzoyl)piperidin-1-yl]butyl]-3,4,5,7,8,9-hexahydrothieno[4,3,2-de]pyrido[1,2-c]pyrimidine-3,5,9-trione The title compound was prepared by starting with 3-[4-[4-(4-fluorobenzoyl)piperidin-1-yl]butyl]-thieno[3,4-d]pyrimidine-2,4-dione. This material (2.91 g, 6.8 mmol) was reacted with methyl acrylate as described in Example 1 using DMF as the solvent to produce 2.26 g (64.6%) of methyl 3-[3-[4-[4-(4-fluorobenzoyl)piperidin-1-yl]butyl]-2,4-dioxothieno[3,4-d]pyrimidin-1-yl]propanoate as a creamed-colored solid after trituration with ether/hexane, mp 102.5°-103.5° C.

Theor. $C_{26}H_{30}FN_3O_5S$: C,60.57;H,5.86;N,8.15. Found: C,60.49;H,5.90;N,8.13.

The above ester (1.6 g, 3.1 mmol) was hydrolyzed to its corresponding carboxylic acid as described in Example 1. There was obtained 1.35 g (86.7%) of 3-[3-[4-[4-(4-fluorobenzoyl)piperidin-1-yl]butyl]-2,4-dioxo-thieno[3,4-d]pyrimidin-1-yl]propanoic acid after trituration with ether.

The above crude acid was cyclized as in Example 1. There was obtained 1.01 g (77.6%) of the title compound after recrystallization from $CH_2Cl_2$/hexane as a paleorange solid, mp 184°-185° C.

Theor. $C_{25}H_{26}FN_3O_4S$: C,62.10;H,5.42;N,8.69. Found: C,61.88;H,5.45;N,8.57.

EXAMPLE 43

4-[5-[4-(3-Trifluoromethylphenyl)piperazin-1-yl]pentyl]-3,4,5,7,8,9-hexahydrothieno]4,3,2-de]pyrido[1,2-c]pyrimidine-3,5,9-trione The title compound was prepared by the procedure in Example 18 starting with 10.13 g (29 mmol) of the N-(5-bromopentyl)-N'-(4-carbomethoxythien-3-yl)urea of Example 12 and 15.47 g (58 mmol) of 1-(3-trifluoromethylphenyl)piperazine hydrochloride. There was obtained 13.08 g (96%) of the known 3-[5-[4-(3-trifluoromethylphenyl)piperazin-1-yl]pentyl]thieno[3,4- d]pyrimidine-2,4-dione (J. Press and R. Russell, U.S. Pat. No. 4,670,560) which was crystallized from $CH_2Cl_2$/hexane to afford a white solid, mp 118°–123° C.

Theor. $C_{22}H_{25}F_3N_4O_2S$: C,56.64;H,5.40;N,12.01. Found: C,56.68;H,5.56;N,11.96.

The title compound was produced following the procedure of Example 1 using 12.0 g (26 mmol) of 3-[5-[4-(3-trifluoromethylphenyl)piperazin-1-yl]pentyl]-thieno[3,4-d]pyrimidine-2,4-dione in DMF at 50° C. for 24 hours to produce methyl 3-[3-[5-[4-(3-trifluoromethylphenyl)piperazin-1-yl]pentyl]-2,4-dioxothieno[3,4-d]pyrimidin-1-yl]propanoate in 41% yield (5.78 g) after recrystallization from ether/hexane, mp 99.5°–101° C.

Theor. $C_{26}H_{31}F_3N_4O_4S$: C,56.51;H,5.65;N,10.14. Found: C,56.81;H,5.77;N,10.10.

The above ester (5.08 g, 9.2 mmol) was hydrolyzed to its corresponding carboxylic acid as described in Example 1. There was obtained 5.23 g (>100%) of 3-[3-[5-[4-(3-trifluoromethylphenyl)piperazin-1-yl]pentyl]-2,4-dioxothieno[3,4-d]pyrimidin-1-yl]propanoic acid as a white solid.

The above crude acid was cyclized as described in Example 1. There was obtained 2.11 g (42%) of the title compound after recrystallization from $CH_2Cl_2$/ether/hexane as a yellow solid, mp 128°–131° C.

Theor. $C_{25}H_{27}F_3N_4O_3S$: C,57.68;H,5.23;N,10.76. Found: C,57.64;H,5.32;N,10.59.

EXAMPLE 44

4-[5-[4-(3-Trifluoromethylphenyl)piperazin-1-yl]-pentyl]-3,4,5,7,8,9-hexahydro-9-methoxyiminothieno[4,3,2-de]pyrido[1,2-c]pyrimidine-3,5-dione The title compound was prepared by the procedure in Example 26 starting with 0.52 g (1.0 mmol) of the trione from Example 43 and 167 mg (2.0 mmol) of O-methylhydroxylamine hydrochloride. There was obtained 340 mg (61.8%) of the title compound as a yellow solid after recrystallization from $CH_2Cl_2$/ether/hexane, mp 107°–110° C.

Theor. $C_{26}H_{30}F_3N_5O_4S$: C,56.82;H,5.50;N,12.74. Found: C,57.19;H,5.61;N,12.75.

EXAMPLE 45

4-[5-[4-[Bis(4-fluorophenyl)methylene]piperadin-1-yl]pentyl]-3,4,5,7,8,9-hexahydrothieno[4,3,2-de]pyrimidine-3,5,9-trione Monooxalate The title compound was prepared by starting with 3-[5-[4-(bis(4-fluorophenyl)methylene]piperidin-1-yl]pentyl]thieno[3,4-d]pyrimidine-2,4-dione. This material (11.0 g, 21 mmol) was reacted with methyl acrylate as described in Example 1 to produce 8.06 g (57%) of methyl 3-[3-[5-[4-[bis(4-fluorophenyl)methylene]piperidin-1-yl]pentyl]-2,4-dioxothieno[3,4-d]pyrimidin-1-yl]propanoate as a yellow oil. A portion of this material was converted to its crystalline oxalate salt by dissolving in acetone and treating with 1.1 equivalents of oxalic acid. There was obtained a cream-colored solid, mp 129°–136° C.

Theor. $C_{33}H_{35}F_2N_3O_4S.C_2H_2O_4$: C,60.25;H,5.34;N,6.02. Found: C,60.26;H,5.38;N,5.96.

The above ester (6.41 g, 10 mmol) was hydrolyzed to its corresponding carboxylic acid as described in Example 1. There was obtained 6.23 g (99%) of 3-[3-[5-[4-[bis(4-fluorophenyl)methylene]piperidin-1-yl]pentyl]-2,4-dioxothieno[3,4-d]pyrimidin-1-yl]propanoic acid.

The above crude acid (6.23 g, 10 mmol) was cyclized as in Example 1. There was obtained 1.90 g (29%) of the title compound after the oily product had been converted to its gray oxalate salt, mp 142° C. (dec.).

Theor. $C_{32}H_{31}F_2N_3O_3S.C_2H_2O_4$: C,61.34;H,4.99;N,6.31. Found: C,61.63;H,5.06;N,6.30.

EXAMPLE 46

Preparation of Starting Material

3-[4-[4-(4-Fluorobenzoyl)piperidin-1-yl]-butyl]-thieno[3,4-d]pyrimidine-2,4-dione The title compound was prepared by dissolving N-(4-bromobutyl)-N'-(4-carbomethoxythien-3-yl)urea (6.92g, 21 mmol) in isopropanol (100 ml) and then successively treating the solution with 4-(4-fluorobenzoyl)-piperidine hydrochloride (10.16 g, 42 mmol), sodium bicarbonate (3.7 g, 44 mmol) and sodium iodide (1.90 g, 12 mmol) to form a mixture. The urea was prepared by reacting methyl 4-aminothiophene-3-carboxylate with 4-bromobutylisocyanate in toluene at room temperature for 12 hours to produce the urea as a tan solid, mp 85°–86° C. The mixture was then heated to reflux under a nitrogen atmosphere for 12 hours. The reaction mixture was reduced to half volume, diluted with water, and concentrated to remove the remainder of the alcohol solvent. The residue was extracted with methylene chloride and the combined organic extracts were dried with saturated brine and magnesium sulfate. After concentration of the extracts, the residue was purified on silica gel using methylene chloride/ethanol/ammonium hydroxide (96:3.5:0.5) as eluant. There was obtained 3.62 g (40.8% yield) of the title compound as a brown solid. This material was recrystallized from $CH_2Cl_2$/ether, mp 190°–192° C.

Theor. $C_{22}H_{24}FN_3O_3S$: C,61.52;H,5.63;N,9.78. Found: C,61.58;H,5.63;N,9.73.

EXAMPLE 47

Preparation of Starting Material

3-[5-[4-[Bis(4-fluorophenyl)methylene]piperidin-1-yl]pentyl]thieno]3,4-d]pyrimidine-2,4-dione The title compound was prepared by the procedure of Example 46 using N-(5-bromopentyl)-N'-(4-carbomethoxythien-3-yl)urea (9.01 g, 26 mmol) and 4-[bis(4-fluorophenyl)methylene]piperidine (14.76 g, 52 mmol). The urea was prepared by reacting methyl 4-aminothiophene-3-carboxylate with one equivalent of 5-bromopentylisocyanate in toluene at room temperature for four hours to produce the urea as a tan solid (98% yield). This material was recrystallized from $CH_2Cl_2$/ether/hexane to afford the urea as a white solid, mp 92°–93.5° C.

Theor. $C_{12}H_{17}BrN_2O_3S$: C,41.26;H,4.91;N,8.02. Found: C,41.52;H,4.94;N,7.98.

There was obtained 12.04 g (89% yield) of the title compound as a cream-colored solid after recrystallization from $CH_2Cl_2$/ether/hexane, mp 118°–122° C.

Theor. $C_{29}H_{29}F_2N_3O_2S$: C,66.77;H,5.60;N,8.06. Found: C,66.38;H,5.44;N,7.97.

EXAMPLE 48

Antihypertensive Activity: Spontaneously Hypertensive Rat

Groups of three to four male spontaneously hypertensive rats (SHR) with mean arterial blood pressures equal to or greater than 150 mmHg (or within two standard deviations of the established control population) were used to evaluate compounds for antihypertensive activity. Mean arterial pressure and heart rate were monitored from directly cannulated animals. Compounds were administered p.o. or i.v. and blood pressure was recorded for various time intervals post dosing.

Blood pressure changes (expressed as change in control pressure and reported as delta % of control for each animal) were analyzed statistically using a one way analysis of variance with a Dunnett's test. P values less than 0.05 were considered significant. The results for representative compounds are shown in Table I, below.

EXAMPLE 49

Brain Alpha-1 Radioreceptor Assay

Membrane fragments were prepared from the brains of mature female guinea pigs after removal of the corpus striata. The alpha-1 adrenergic receptor sites were labeled with $^3$H-prazosin. Membrane fragments, $^3$H-prazosin and an unlabeled test compound were incubated for 30 minutes at 30° C. Compound bound to the receptor site was separated from the remaining unbound radioligand by vacuum filtration. Specific binding was determined by the difference between total counts bound and counts bound in the presence of $10^{-5}$M phentolamine. The results for representative compounds are shown in Table I, below.

EXAMPLE 50

Brain Serotonin 5HT$_2$ Radioreceptor Assay

Membrane fragments were prepared from the frontal cortex dissected from brains obtained from female rats (~150 g). The 5HT$_2$ sites were labeled with $^3$H-ketanserin. Membrane fragments, $^3$H-ketanserin and an unlabeled test compound were incubated for 15 minutes at 37° C. Compound bound to the receptor site was separated from the remaining unbound compound by vacuum filtration.

The ability of a nonlabeled compound to compete with $^3$H-ketanserin for binding sites was a measure of the compound's affinity for the 5HT$_2$ receptor. Specific binding was determined by the difference between total counts bound and counts bound in the presence of $10^{-6}$M methysergide.

Data are presented as the IC$_{50}$, the concentration of nonlabeled compound required to displace 50% of the $^3$H-ketanserin specifically bound to 5HT$_2$ binding sites. The results for representative compounds are shown in Table I, below.

EXAMPLE 51

Brain Serotonin 5HT$_{1A}$ Radioreceptor Assay

Membrane fragments were prepared from the frontal cortex dissected from brains obtained from female rats (~150 g). The 5HT$_{1A}$ sites were labeled with $^3$H-8OH-dipropylaminotetralin ($^3$H-8OH-DPAT). Membrane fragments, $^3$H-8OH-DPAT and an unlabeled test compound were incubated for 10 minutes at 37° C. The tubes were then placed in an ice bath for an additional 10 minutes. Compound bound to the receptor site was separated from the remaining unbound compound by vacuum filtration.

The ability of a nonlabeled compound to compete with $^3$H-8OH-DPAT for binding sites was a measure of the compound's affinity for the 5HT$_{1A}$ receptor. Specific binding was determined by the difference between total counts bound and counts bound in the presence of $10^{-5}$M serotonin.

Data are presented at the IC$_{50}$, the concentration of nonlabeled compound required to displace 50% of the $^3$H-8OH-DPAT specifically bound to 5HT$_{1A}$ binding sites. The results for representative compounds are shown in Table I, below.

EXAMPLE 52

Alpha-1 Adrenergic Blockage: Inhibition of Phenylephrine-Induced Increases in Blood Pressure in the Anesthetized Dog Dogs were anesthetized and bilaterally vagotomized. A femoral artery and vein were cannulated for detection of diastolic blood pressure and drug administration, respectively. Percent inhibition of alpha adrenergic receptor antagonism was quantified by determining dose-response (increase in diastolic pressure) relationship of phenylephrine before and after various doses of the antagonist. The percent inhibition of alpha adrenergic receptor antagonism was quantified by measuring the percent inhibition of the pressor response to 10 μg/kg of phenylephrine. The results for representative compounds are shown in Table I, below.

TABLE I

| COMPOUND (Example) | SHR TEST (DOSE, MPK) | RECEPTOR BINDING (IC50, MICROMOLAR) ALPHA-1 | 5HT-2 | 5HT-1A | % INHIB OF PHENYLEPHRINE RESPONSE [Dose (mpk), i.v.] |
|---|---|---|---|---|---|
| 1 | −59 mm Hg (2.5) | 0.018 | 6.5 | 0.025 | 86% (0.03) |
| 2 | −33% (5) | | | | 83% (0.03) |
| 3 | | | | | 55% (0.03) |
| 4 | | | | | 88% (0.03) |
| 5 | | | | | 41% (0.03) |
| 6 | | 1 | 0.7 | 0.028 | |
| 7 | | 0.18 | 0.35 | 0.005 | |
| 8 | | | | | 40% (0.03) |
| 9 | −21.5% (5) | | | | |
| 10 | | 0.021 | 0.3 | 0.005 | |
| 11 | | 0.0005 | 33% @ $10^{-6}$ | 0.0009 | |
| 12 | | | 1.5 | 0.045 | |
| 13 | | | | | 88% (0.03) |
| 14 | −30.0% (5) | 0.006 | 1.5 | 0.066 | |
| 15 | −29.8% (5) | | | | |
| 16 | | 0.035 | 2 | 0.16 | |
| 17 | | 0.0076 | 21% @ $10^{-6}$ | 1.8% @ $10^{-6}$ | |
| 18 | | 4.5 | 47% @ $10^{-6}$ | | |
| 19 | | 1 | 0.001 | 35% @ $10^{-6}$ | |

TABLE I-continued

| COMPOUND (Example) | SHR TEST (DOSE, MPK) | RECEPTOR BINDING (IC50, MICROMOLAR) | | | % INHIB OF PHENYLEPHRINE RESPONSE [Dose (mpk), i.v.] |
|---|---|---|---|---|---|
| | | ALPHA-1 | 5HT-2 | 5HT-1A | |
| 20 | | 22 | 0.18 | 47% @ $10^{-6}$ | |
| 21 | −24.7% (5) | | | | 96% (0.03) |
| 22 | | 0.0004 | 0.27 | 0.062 | |
| 23 | −27.4% (5) | | | | |
| 24 | −59.0 mm Hg (2.5) | 0.023 | 2 | 0.12 | 98% (0.03) |
| 25 | −58.0 mm Hg (2.5) | 0.045 | 2 | 0.048 | 94% (0.003) |
| 26 | | 0.04 | 2 | 0.00072 | 72% (0.03) |
| 27 | | 0.00014 | 11% @ $10^{-6}$ | 0.07 | |
| 28 | | <0.001 | 0.15 | 0.02 | |
| 29 | | 0.026 | 34.3% @ $10^{-6}$ | 5.2% @ $10^{-6}$ | |
| 30 | −33.2% (5) | | | | 100% (0.03) |
| 31 | | | | | 100% (0.03) |
| 32 | | | | | 90% (0.03) |
| 33 | −32% (5) | | | | |
| 34 | −26% (5) | | | | |
| 35 | −16.6% (5) | 0.000015 | 1.5 | 0.13 | 89% (0.03) |
| 36 | −14.0% (5) | | | | |
| 37 | −30.2% (5) | | | | |
| 38 | −30.1% (2.5) | 0.01 | 0.8 | 0.05 | |
| 39 | | 0.00035 | 0.75 | 0.58 | |
| 40 | | 0.003 | 2.5 | 45% @ $10^{-5}$ | |
| 41 | | 40 | 1 | 1 | |
| 42 | | 0.54 | 0.63 | 0.4 | |
| 43 | | | 0.43 | 0.052 | |
| 44 | | | 0.13 | 0.2 | |
| 45 | | | 0.055 | 0.24 | |

What is claimed is:

1. A compound of the formula

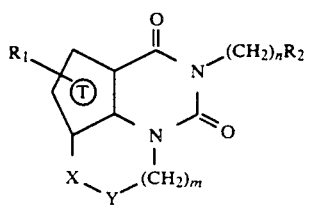

where X is C=O or CHOR$_3$ or C=NOR$_4$ or CHNHR$_3$ when Y is CH$_2$ or X and Y together are CH=CH or Y is NH when X is C=O

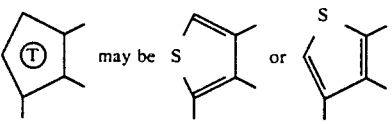

R$_1$ is hydrogen, halogen, nitro or C$_1$–C$_3$ alkyl
R$_2$ is

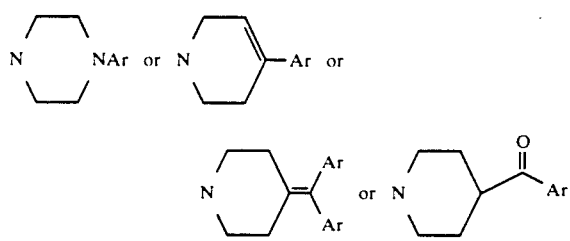

R$_3$ is hydrogen, C$_1$–C$_3$ alkyl or COR$_5$;
R$_4$ is hydrogen or C$_1$–C$_6$ alkyl;
R$_5$ is C$_1$–C$_6$ alkyl, phenyl or phenyl substituted by halogen, C$_1$–C$_6$ alkyl, C$_1$–C$_3$ alkoxy, nitro, CF$_3$, amino or C$_1$–C$_6$ dialkylamino;
Ar is phenyl or phenyl substituted by halogen, C$_1$–C$_6$ alkyl, C$_1$–C$_3$ alkoxy, nitro, CF$_3$, amino or C$_1$–C$_6$ dialkylamino;
m is 1–5; and
n is 2–6

2. The compound of claim 1 wherein
R$_1$ is hydrogen or C$_1$–C$_3$ alkyl;
R$_3$ is hydrogen or COR$_5$;
R$_4$ is hydrogen or methyl;
R$_5$ is C$_1$–C$_6$ alkyl or phenyl or phenyl substituted by 4-chloro or 4-methoxy;
Ar is phenyl or phenyl substituted by halogen, methyl, methoxy or CF$_3$;
m is 1–3; and
n is 2–5.

3. The compound of claim 1 selected from the group consisting of
3,4,5,7,8,9-hexahydro-4-[2-[4-(2-methoxyphenyl)piperazin-1-yl]ethyl]thieno[4,3,2-de]pyrido[1,2-c]pyrimidine-3,5,9-trione;
3,4,5,7,8,9-hexahydro-4-[2-[4-(2-methylphenyl)piperazin-1-yl]ethyl]thieno[4,3,2-de]pyrido[1,2-c]pyrimidine-3,5,9-trione;
3,4,5,7,8,9-hexahydro-4-[2-(4-phenylpiperazin-1-yl)ethyl]thieno[4,3,2-de]pyrido[1,2-c]pyrimidine-3,5,9-trione;
4-[2-[4-(3-trifluoromethylphenyl)piperazin-1-yl]ethyl]-3,4,5,7,8,9-hexahydrothieno[4,3,2-de]pyrido[1,2-c]pyrimidine-3,5,9-trione;
4-[2-[4-(3-chlorophenyl)piperazin-1-yl]ethyl]-3,4,5,7,8,9-hexahydrothieno[4,3,2-de]pyrido[1,2-c]pyrimidine-3,5,9-trione;
3,4,5,7,8,9-hexahydro-4-[3-[4-(2-methoxyphenyl)piperazin-1-yl]propyl]thieno[4,3,2-de]pyrido[1,2-c]pyrimidine-3,5,9-trione;

3,4,5,7,8,9-hexahydro-4-[4-[4-(2-methoxyphenyl)piperazin-1-yl]butyl]thieno[4,3,2-de]pyrido[1,2-c]pyrimidine-3,5,9-trione;

3,4,5,7,8,9-hexahydro-4-[5-[4-(2-methoxyphenyl)piperazin-1-yl]pentyl]thieno[4,3,2-de]pyrido[1,2-c]pyrimidine-3,5,9-trione;

3,4,5,7,8,9-hexahydro-2-methyl-4-[2-[4-(2-methoxyphenyl)piperazin-1-yl]ethyl]thieno[4,3,2-de]pyrido[1,2-c]pyrimidine-3,5,9-trione;

7,8-dihydro-4-[2-[4-(2-methoxyphenyl)piperazin-1-yl]ethyl]thieno[2,3,4-de]pyrido[1,2-c]pyrimidine-3,5,9-trione;

4,7,8,9-tetrahydro-4-[2-[4-(2-methoxyphenyl)piperazin-1-yl]ethyl]thieno[4,3,2-de]pyrimido[3,4-a]azepine-3,5,10-trione;

4,7,8,9,10,11-hexahydro-4-[2-[4-(2-methoxyphenyl)piperazin-1-yl]ethyl]thieno[4,3,2-de]pyrimido[3,4-a]azocine-3,5,11-trione;

3,4,5,7,8,9-hexahydro-4-[2-(4-phenyl-1,2,3,6-tetrahydropyridin-1-yl)ethyl]thieno[4,3,2-de]pyrido[1,2-c]pyrimidine-3,5,9-trione;

4-[2-[4-(4-fluorobenzoyl)piperidin-1-yl]ethyl]-3,4,5,7,8,9-hexahydrothieno[4,3,2-de]pyrido[1,2-c]pyrimidine-3,5,9-trione;

4-[2-[4-[bis(4-fluorophenyl)methylene]piperidin-1-yl]ethyl]-3,4,5,7,8,9-hexahydrothieno[4,3,2-de]pyrimidine-3,5,9-trione;

3,4,5,7,8,9-hexahydro-9-hydroxy-4-[2-[4-(2-methoxyphenyl)piperazin-1-yl]ethyl]thieno[4,3,2-de]pyrido[1,2-c]pyrimidine-3,5-dione;

10-hydroxy-4,7,8,9-tetrahydro-4-[2-[4-(2-methoxyphenyl)piperazin-1-yl]ethyl]thieno[4,3,2-de]pyrimido[3,4-a]azepine-3,5-dione;

3,4,5,7-tetrahydro-4-[2-[4-(2-methoxyphenyl)piperazin-1-yl]ethyl]thieno[4,3,2-de]pyrido[1,2-c]pyrimidine-3,5-dione;

3,4,5,7,9,10-hexahydro-4-[2-[4-(2-methoxyphenyl)piperazin-1-yl]ethyl]-9H-thieno[4,3,2-de]pyrimido[1,2-a]1,4]diazepine-3,5,10-trione;

3,4,5,7,8,9-hexahydro-9-methoxyimino-4-[2-[4-(2-methoxyphenyl)piperazin-1-yl]ethyl]thieno[4,3,2-de]pyrido[1,2-c]pyrimidine-3,5-dione;

4,7,8,9-tetrahydro-10-methoxyimino-4-[2-[4-(2-methoxyphenyl)piperazin-1-yl]ethyl]thieno[4,3,2-de]pyrimido[3,4-a]azepine-3,5-dione;

3,4,5,7,8,9-hexahydro-9-methoxyimino-4-[2-[4-(2-methoxyphenyl)piperazin-1-yl]ethyl]-2-methylthieno[4,3,2-de]pyrido[1,2-c]pyrimidine-3,5-dione;

3,4,5,7,8,9-hexahydro-9-methoxyimino-4-[3-[4-(2-methoxyphenyl)piperazin-1-yl]propyl]thieno-[4,3,2-de]pyrido[1,2-c]pyrimidine-3,5-dione;

9-acetyloxy-3,4,5,7,8,9-hexahydro-4-[2-[4-(2-methoxyphenyl)piperazin-1-yl]ethyl]thieno[4,3,2,de]-pyrido[1,2-c]pyrimidine-3,5-dione;

3,4,5,7,8,9-hexahydro-4-[2-[4-(2-methoxyphenyl)piperazin-1-yl]ethyl]-9-(butanoyloxy)thieno[4,3,2-de]pyrido[1,2-c]pyrimidine-3,5-dione;

3,4,5,7,8,9-hexahydro-4-[2-[4-(2-methoxyphenyl)piperazin-1-yl]ethyl]-9-(hexanoyloxy)thieno[4,3,2-de]pyrido[1,2-c]pyrimidine-3,5-dione;

3,4,5,7,8,9-hexahydro-9-(2-methylpropanoyloxy)-4-[2-[4-(2-methoxyphenyl)piperazin-1-yl]ethyl]thieno[4,3,2-de]pyrido[1,2-c]pyrimidine-3,5-dione;

9-benzoyloxy-3,4,5,7,8,9-hexahydro-4-[2-[4-(2-methoxyphenyl)piperazin-1-yl]ethyl]thieno[4,3,2-de]pyrido[1,2-c]pyrimidine-3,5-dione;

9-(4-chlorobenzoyloxy)-3,4,5,7,8,9-hexahydro-4-[2-[4-(2-methoxyphenyl)piperazin-1-yl]ethyl]thieno[4,3,2-de]pyrido[1,2-c]pyrimidine-3,5-dione;

9-amino-3,4,5,7,8,9-hexahydro-4-[2-[4-(2-methoxyphenyl)piperazin-1-yl]ethyl]thieno[4,3,2-de]pyrido[1,2-c]pyrimidine-3,5-dione;

9-acetylamino-3,4,5,7,8,9-hexahydro-4-[2-[4-(2-methoxyphenyl)piperazin-1-yl]ethyl]thieno[4,3,2-de]pyrido[1,2-c]pyrimidine-3,5-dione;

9-benzoylamino-3,4,5,7,8,9-hexahydro-4-[2-[4-(2-methoxyphenyl)piperazin-1-yl]ethyl]thieno[4,3,2-de]pyrido[1,2-c]pyrimidine-3,5-dione;

4-[4-[4-(4-fluorobenzoyl)piperidin-1-yl]butyl]-3,4,5,7,8,9-hexahydrothieno[4,3,2-de]pyrido[1,2-c]pyrimidine-3,5,9-trione;

4-[5-[4-(3-trifluoromethylphenyl)piperazin-1-yl]pentyl]-3,4,5,7,8,9-hexahydrothieno[4,3,2-de]pyrido[1,2-c]pyrimidine-3,5,9-trione; and 4-[5-[4-[bis(4-fluorophenyl)methylene]piperadin-1-yl]pentyl]-3,4,5,7,8,9-hexahydrothieno[4,3,2-de]pyrimidine-3,5,9-trione Monooxalate.

4. A pharmaceutical composition comprising as an active ingredient an effective amount of a compound of claim 1 and a suitable pharmaceutical carrier.

5. A pharmaceutical composition comprising as an active ingredient an effective amount of a compound of claim 2 and a suitable pharmaceutical carrier.

6. A pharmaceutical composition comprising as an active ingredient an effective amount of a compound of claim 3 and a suitable pharmaceutical carrier.

7. A process for synthesizing a compound of claim 1 wherein X is C=O and Y is CH$_2$ comprising cyclizing a thienopyrimidine-2,4-dione of the formula

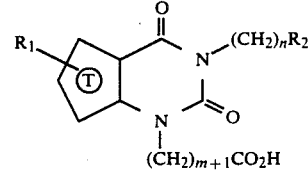

where

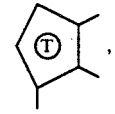

$R_1$, $R_2$, m and n are as defined in claim 1, with a strong dehydrating agent.

8. A process for synthesizing a compound of claim 1 wherein X is C=NOR$_4$ and Y is CH$_2$ comprising mixing a ketone of the formula

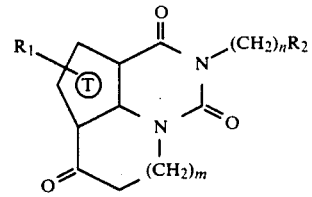

where

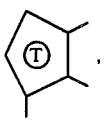

$R_1$, $R_2$, m and n are as defined in claim 1, with a hydroxylamine, a substituted hydroxylamine or a hydroxylamine salt and optionally adding a base.

9. A process for synthesizing a compound of claim 1 wherein X is C=O and Y is NH comprising the use of Beckmann rearrangement conditions to expand the ring structure of an oxime of the formula

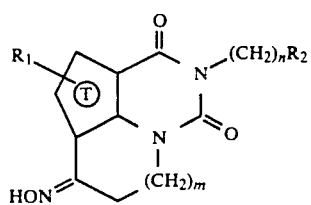

where

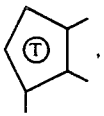

$R_1$, $R_2$, m and n are as defined in claim 1 to the desired compound of the formula

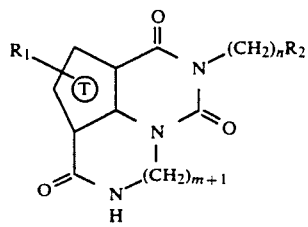

where

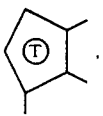

$R_1$, $R_2$, m and n are as defined above.

10. A process for synthesizing a compound of claim 1 wherein X is CHOR$_3$ and Y is CH$_2$ comprising the steps of
(a) reducing a ketone of the formula

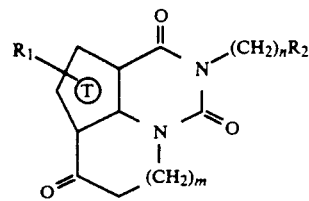

where

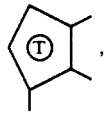

$R_1$, $R_2$, m and n are as defined in claim 1, with a hydride reagent, to produce an alcohol of the formula

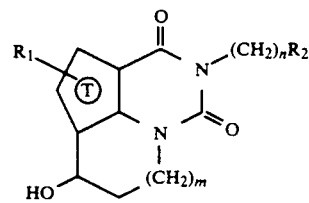

where

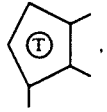

$R_1$, $R_2$, m and n are as defined above; and
(b) optionally alkylating the alcohol with an alkyl halide in an inert solvent in the presence of a base to produce an alkylated compound of the formula

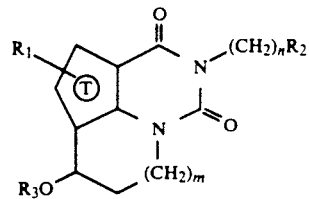

where

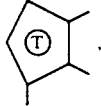

$R_1$, $R_2$, m and n are as defined above and $R_3$ is $C_1$-$C_3$ alkyl or COR$_5$, wherein R$_5$ is as defined in claim 1.

11. A process for synthesizing a compound of claim 1 wherein X and Y together are CH=CH comprising dehydrating an alcohol of the formula

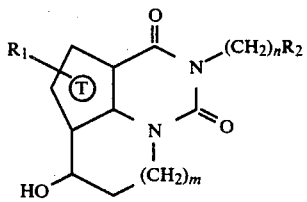

where

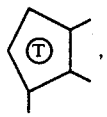

$R_1$, $R_2$, m and n are as defined in claim 1, with a strong acid, acetic acid/acetic anhydride or methanesulfonyl chloride/triethylamine in dichloromethane.

12. A process for synthesizing a compound of claim 1 wherein X is CHNHR$_3$ and Y is CH$_2$ comprising the steps of (a) mixing a ketone of the formula

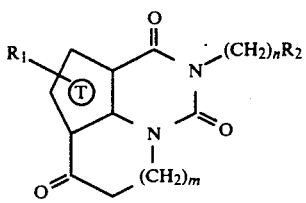

where

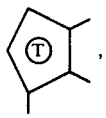

$R_1$, $R_2$, m and n are as defined in claim 1, with a substituted hydroxylamine to produce an oxime of the formula

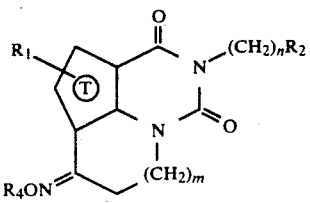

where

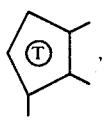

$R_1$, $R_2$, m and n are as defined above and $R_4$ is $C_1$–$C_6$ alkyl;

(b) reducing the oxime with a hydride reagent to produce an amine of the formula

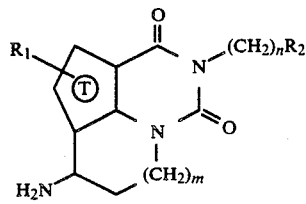

where

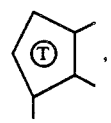

$R_1$, $R_2$, m and n are as defined above; and (c) optionally alkylating the amine with an alkyl halide in an inert solvent in the presence of a base to produce an alkylated amine of the formula

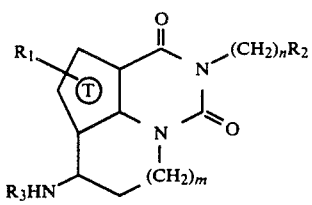

where

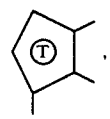

$R_1$, $R_2$, m and n are as defined above and $R_3$ is $C_1$–$C_3$ alkyl; or (d) optionally mixing the amine with an acid halide in an inert solvent to produce an amide of the formula

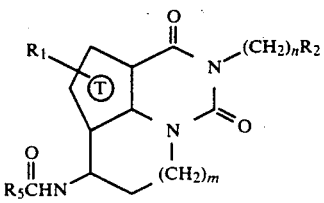

where

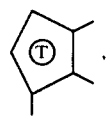

$R_1$, $R_2$, m and n are as defined above and $R_5$ is as defined in claim 1.

13. A method of treating hypertension in mammals by administering an effective amount of a compound of claim 1.

14. A method of treating hypertension in mammals by administering an effective amount of a compound of claim 2.

15. A method of treating hypertension in mammals by administering an effective amount of a compound of claim 3.

16. A method of treating cardiovascular disease in mammals by administering an effective amount of a compound of claim 1.

17. A method of treating cardiovascular disease in mammals by administering an effective amount of a compound of claim 2.

18. A method of treating cardiovascular disease in mammals by administering an effective amount of a compound of claim 3.

* * * * *